United States Patent [19]
Shibata

[11] Patent Number: 6,050,472
[45] Date of Patent: *Apr. 18, 2000

[54] SURGICAL ANASTOMOSIS STAPLER

[75] Inventor: Norikiyo Shibata, Yamato, Japan

[73] Assignee: Olympus Optical Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/840,230

[22] Filed: Apr. 11, 1997

[30]    Foreign Application Priority Data

Apr. 26, 1996  [JP]  Japan ................................. 8-107032
Apr. 26, 1996  [JP]  Japan ................................. 8-107033

[51] Int. Cl.$^7$ ................................................ A61B 17/115
[52] U.S. Cl. ................... 227/175.2; 227/19; 227/176.1; 227/179.1
[58] Field of Search ............................ 227/176.1, 178.1, 227/179.1, 19, 901, 175.2, 175.4; 606/219

[56]                References Cited

U.S. PATENT DOCUMENTS

| | | | |
|---|---|---|---|
| 2,638,901 | 5/1953 | Sugarbaker | 227/19 |
| 4,603,693 | 8/1986 | Conta | 227/179.1 |
| 4,817,847 | 4/1989 | Redtenbacher | 227/19 |
| 4,930,674 | 6/1990 | Barak | 227/179.1 |
| 5,139,513 | 8/1992 | Segato | 227/179.1 |
| 5,197,648 | 3/1993 | Gingold | 227/179.1 |
| 5,205,459 | 4/1993 | Brinkerhoff et al. | 227/19 |
| 5,222,963 | 6/1993 | Brinkerhoff | 606/153 |
| 5,392,979 | 2/1995 | Green et al. | 227/19 |
| 5,597,107 | 1/1997 | Knodel et al. | 227/19 |
| 5,630,539 | 5/1997 | Plyley et al. | 227/175.2 |
| 5,718,359 | 2/1998 | Palmer et al. | 227/175.4 |

FOREIGN PATENT DOCUMENTS 55-108347   8/1980   Japan .

*Primary Examiner*—Peter Vo
*Assistant Examiner*—James P. Calve
*Attorney, Agent, or Firm*—Morgan, Lewis & Bockius LLP

[57]                ABSTRACT

Improved medical suturing apparatus comprises a main body that consists of an operating member and an insertion member extending therefrom and an anvil head that is provided at the distal end of the main body for clinching a plurality of staples, said apparatus further including a staple head that has an array of staples and which is provided in a position opposed to the anvil head.

14 Claims, 29 Drawing Sheets

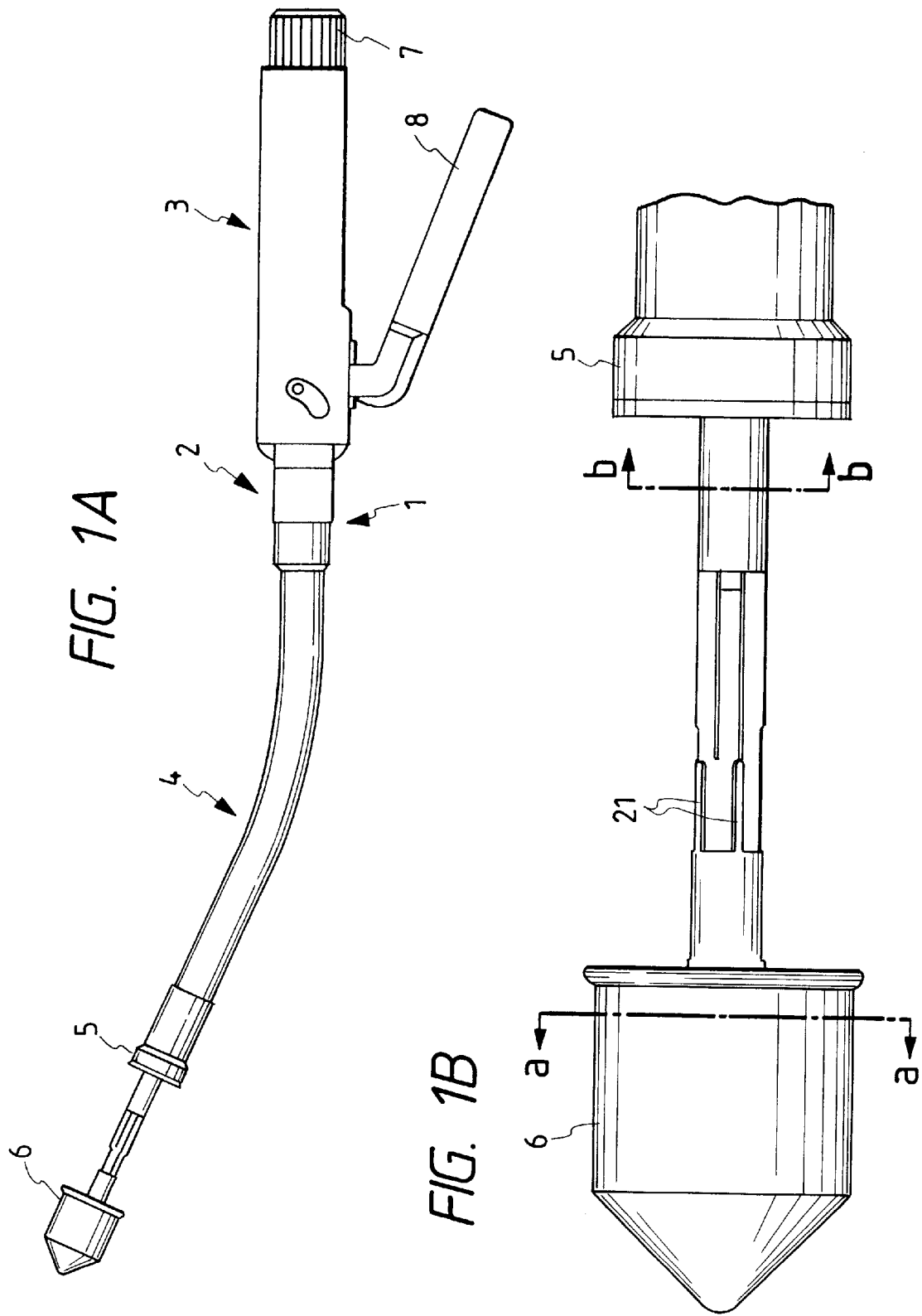

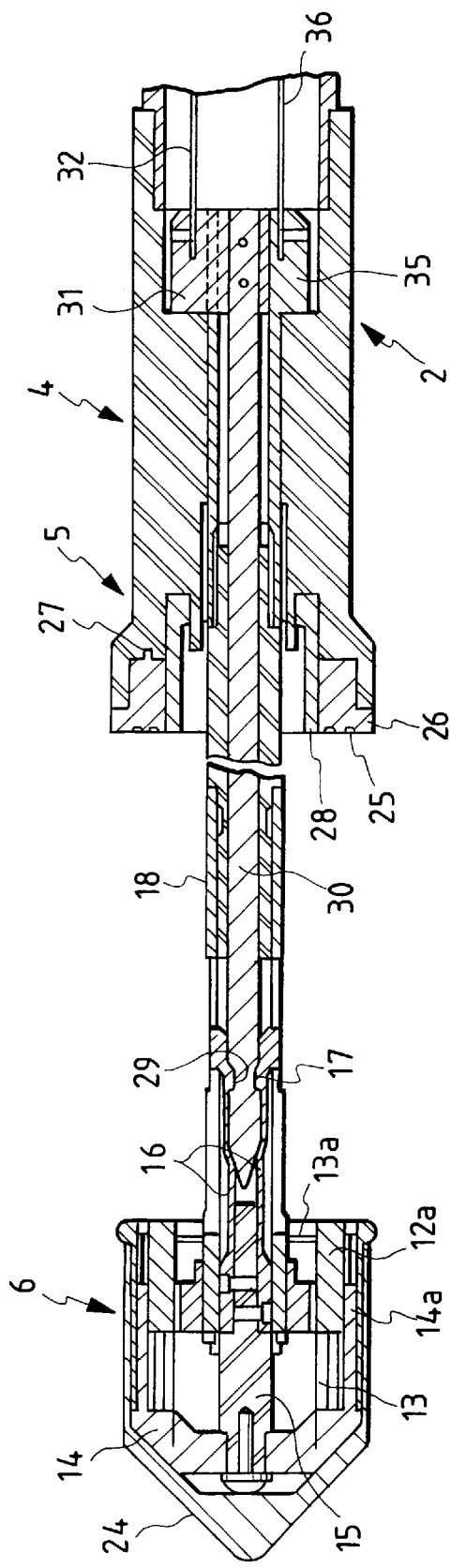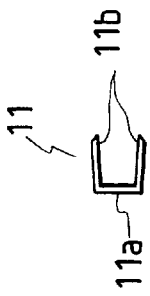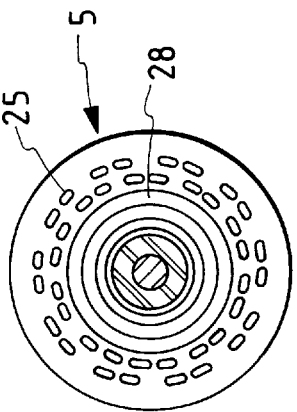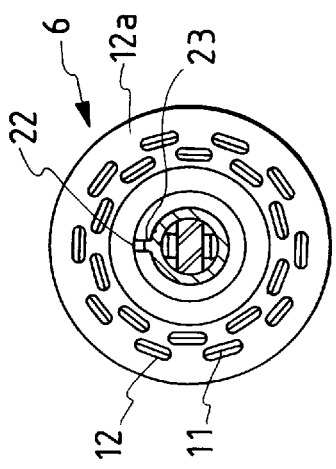
FIG. 2A
FIG. 2B
FIG. 2C
FIG. 2D

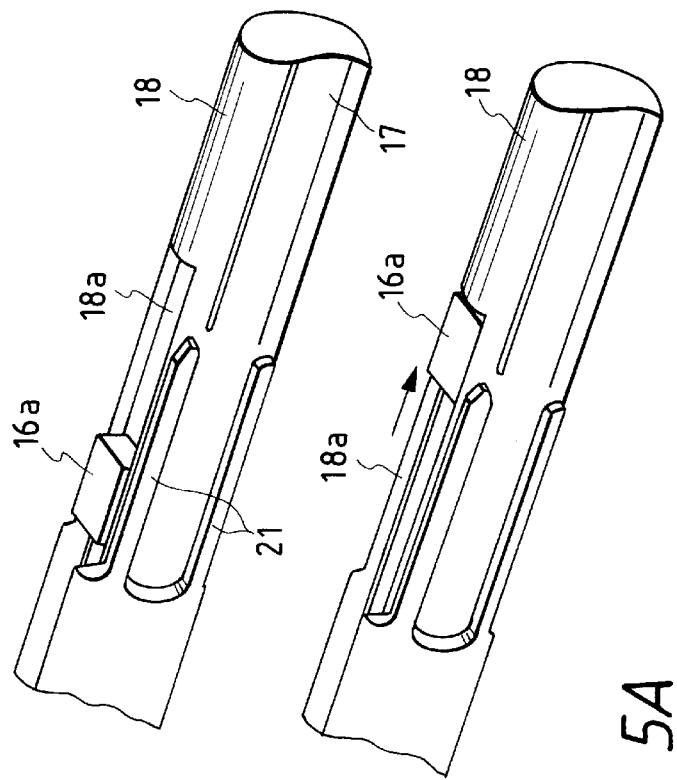
FIG. 4A
FIG. 4B
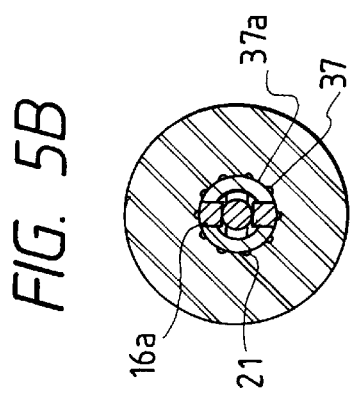
FIG. 5B
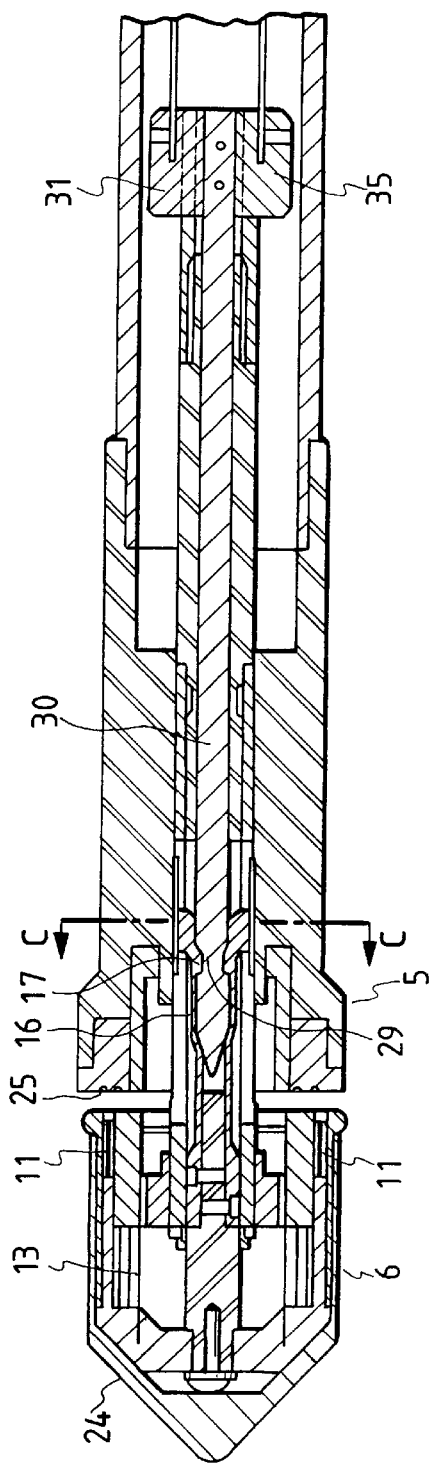
FIG. 5A

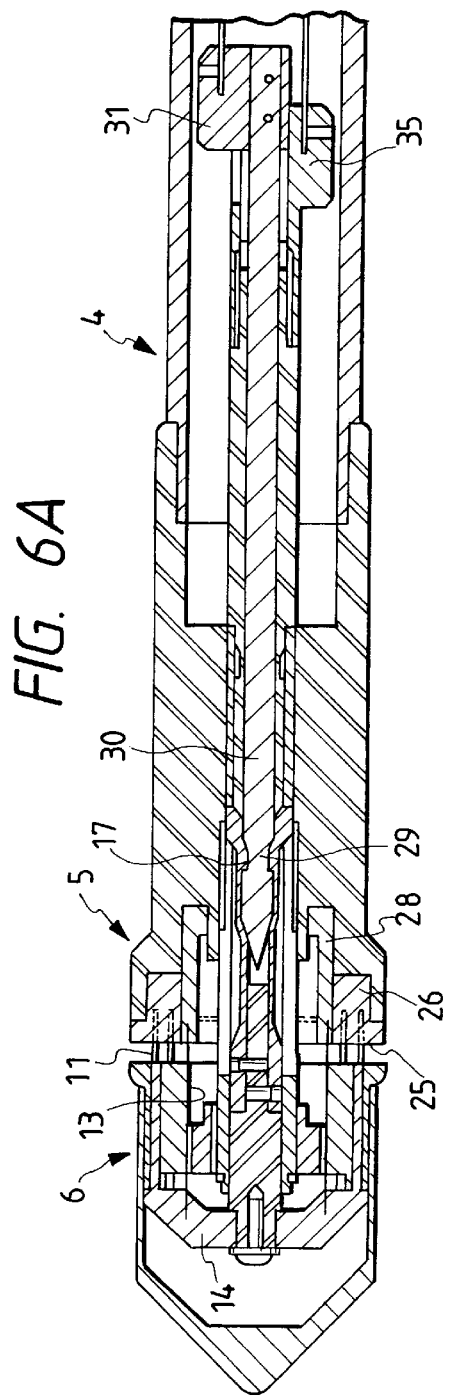
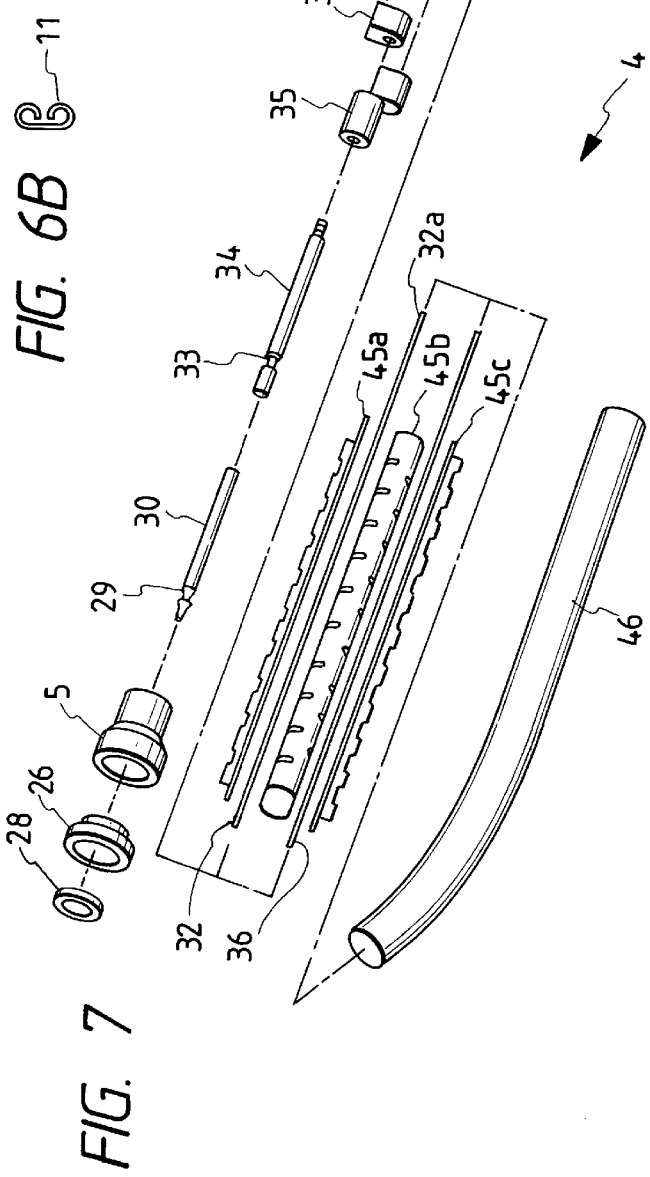
FIG. 6A
FIG. 6B
FIG. 7

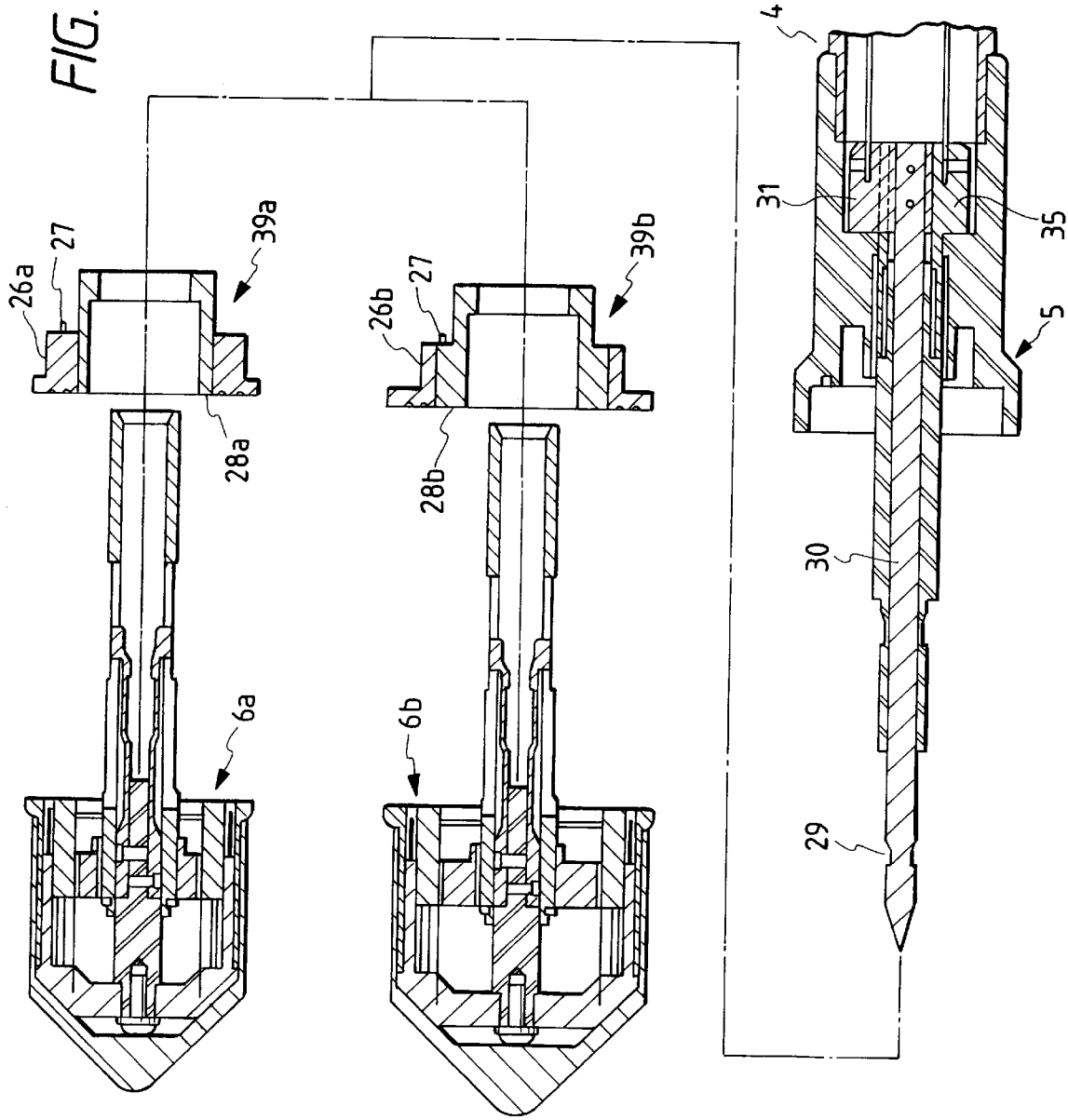

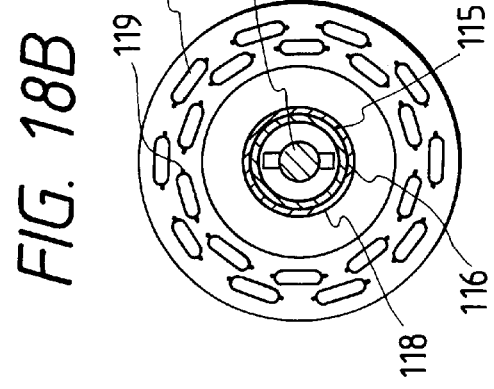
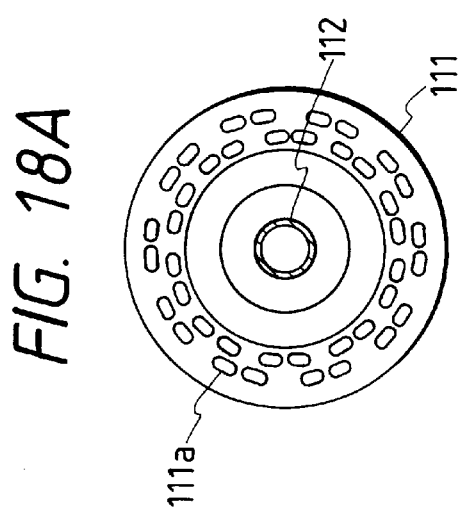
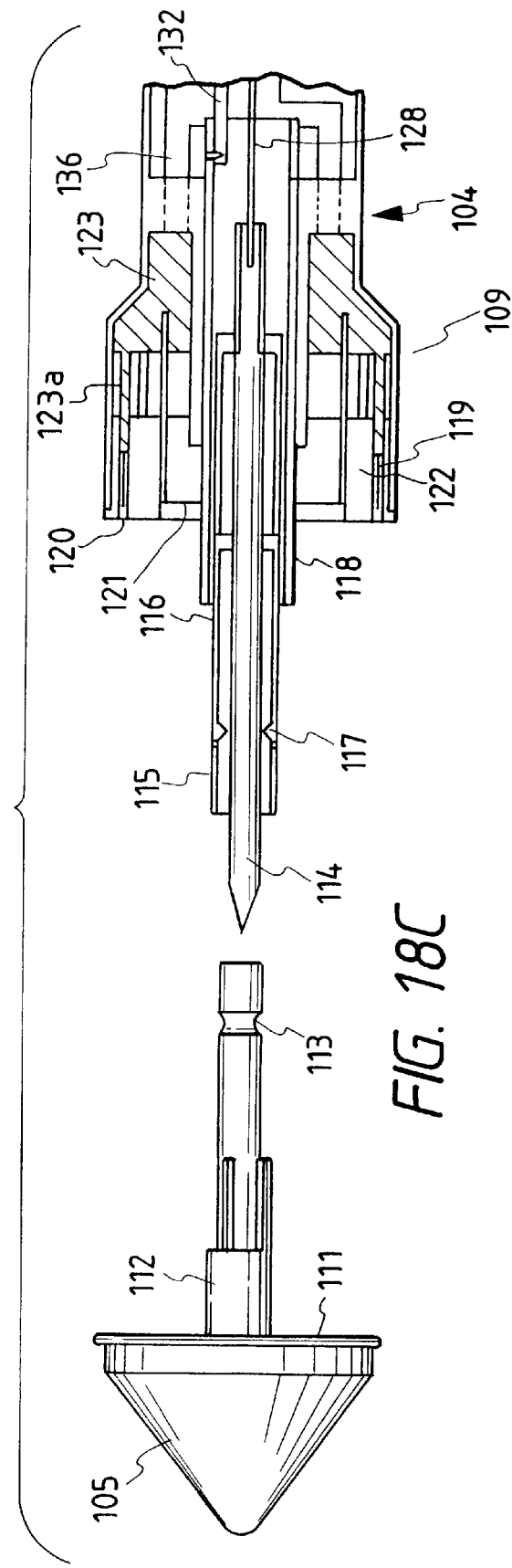

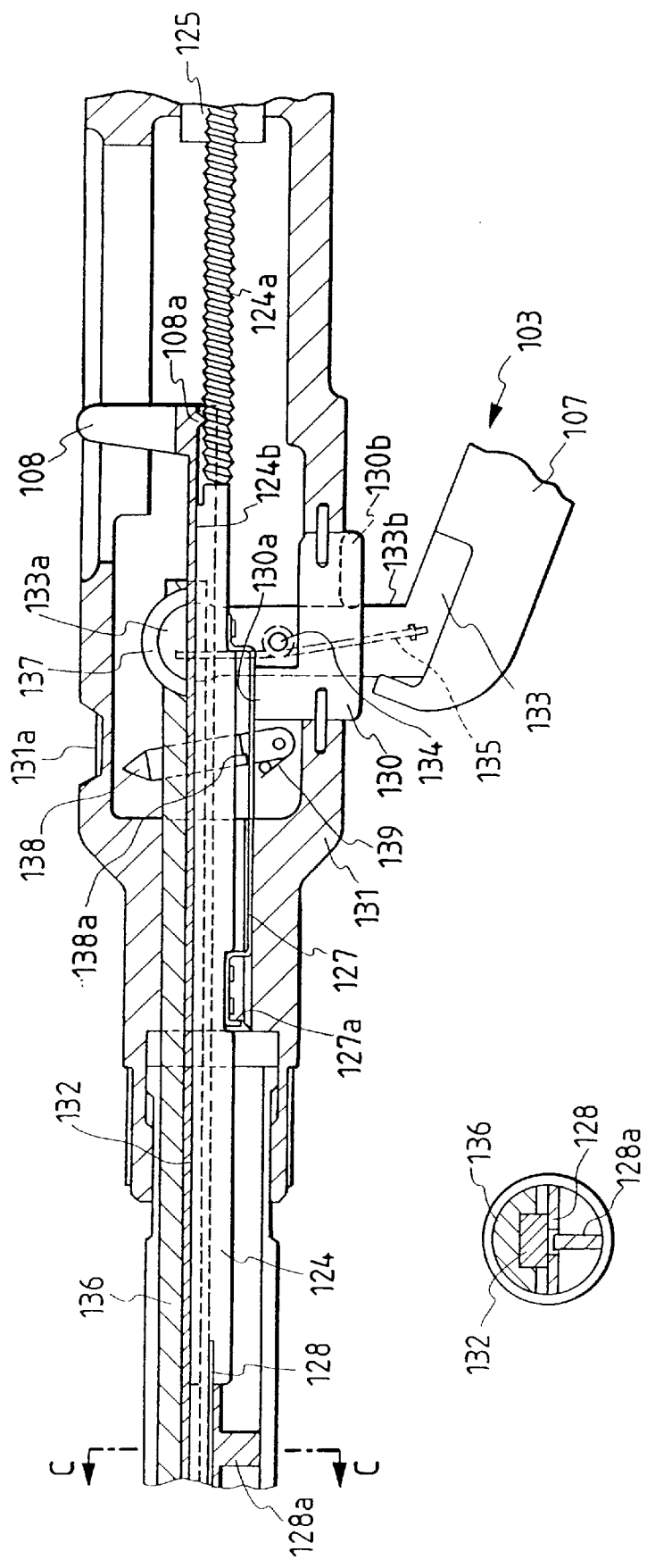

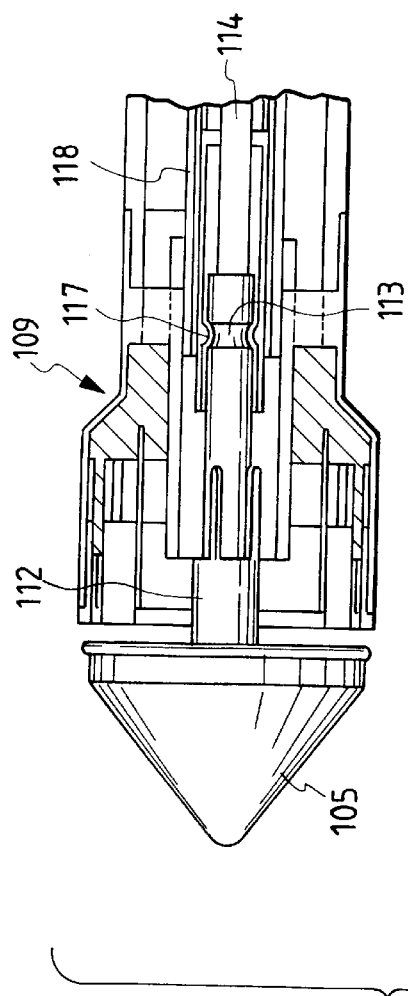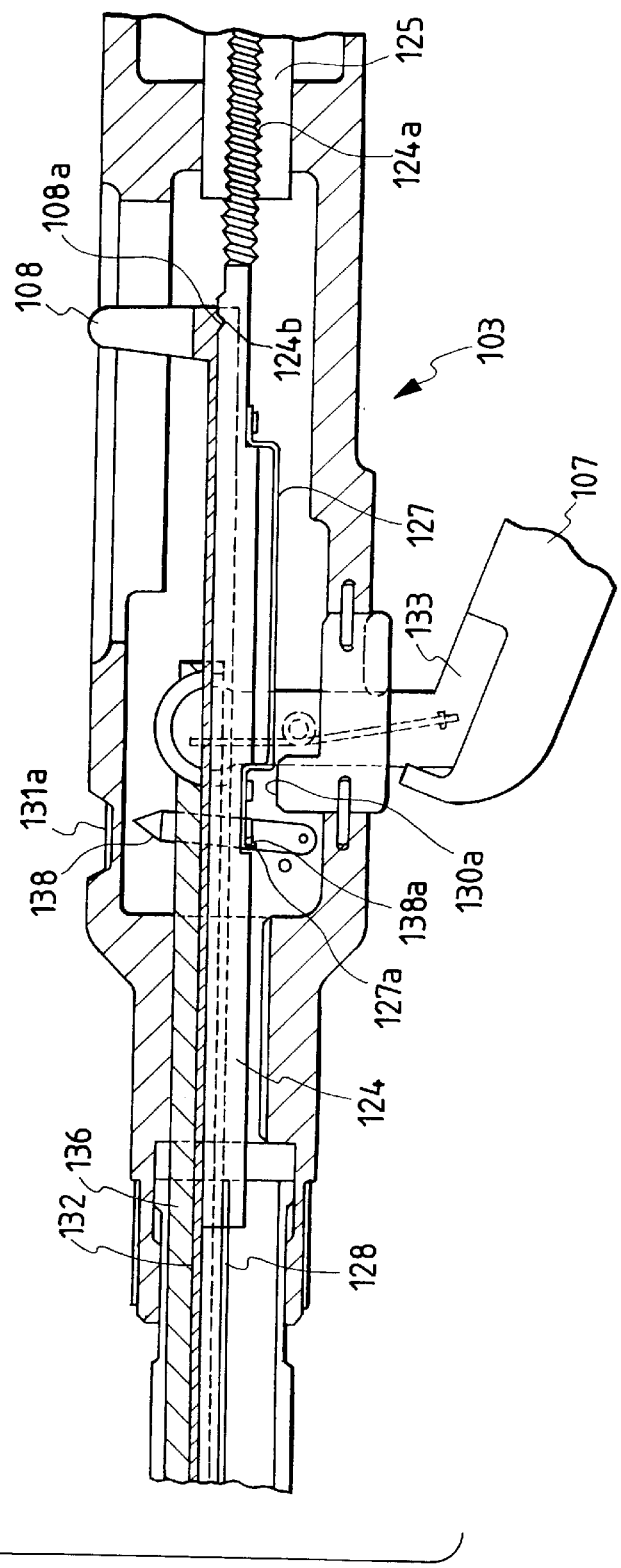
FIG. 22

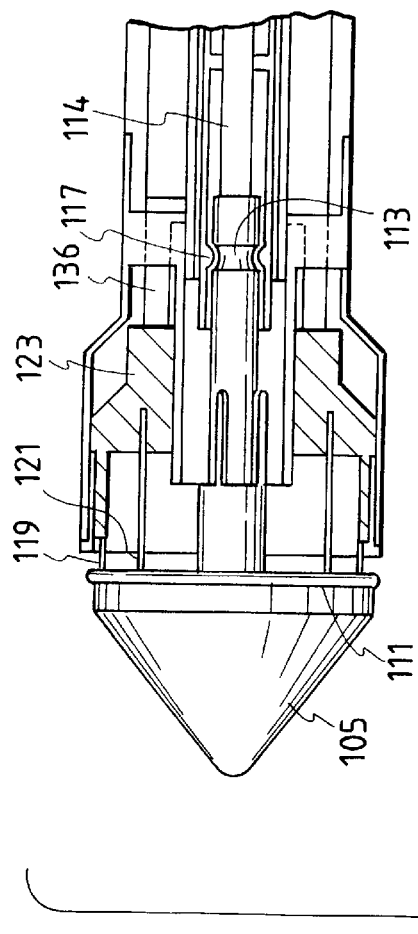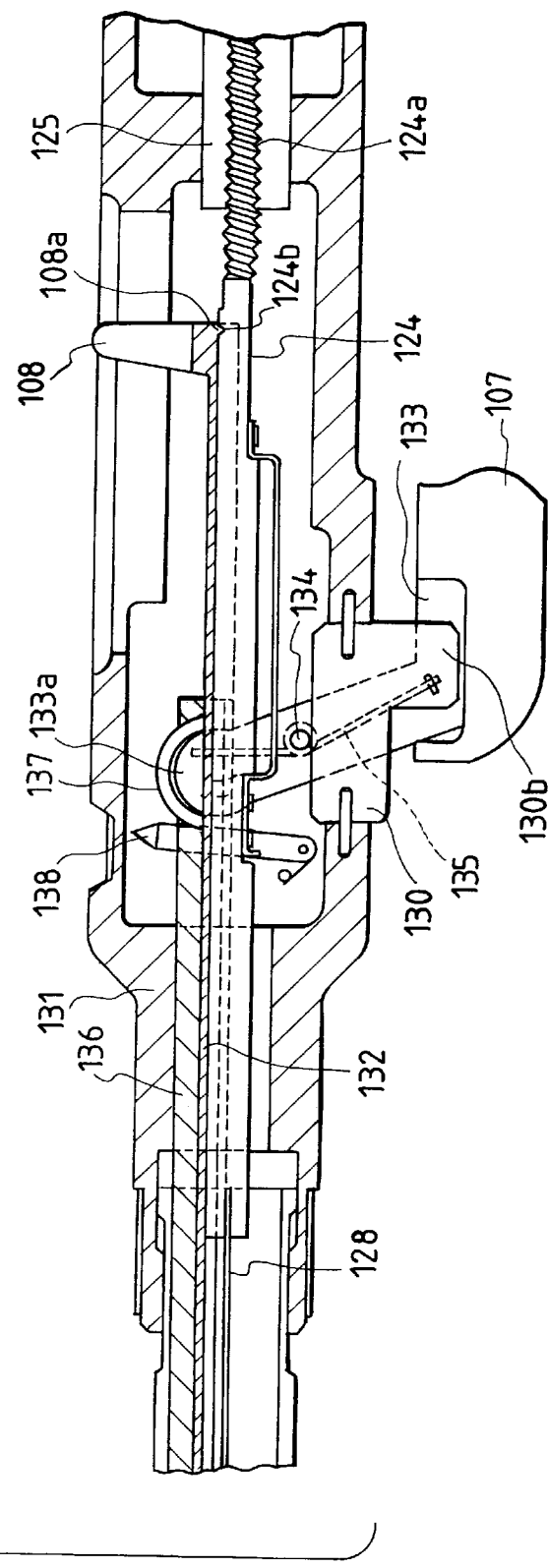
FIG. 23

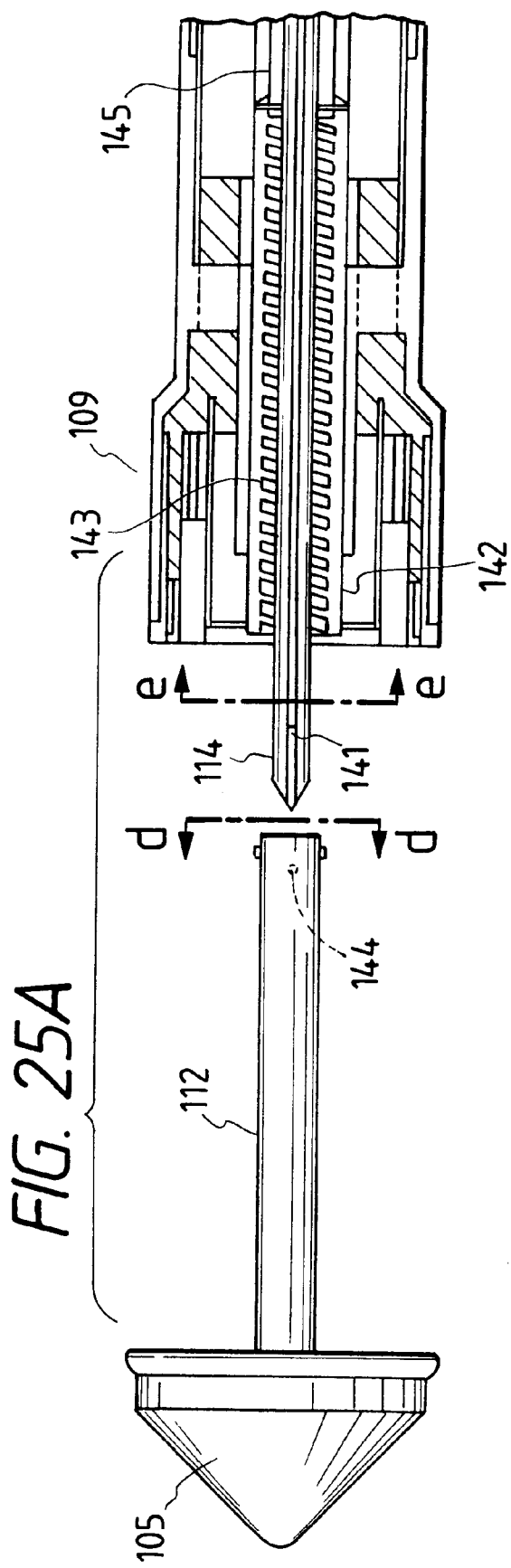
FIG. 25A
FIG. 25B
FIG. 25C

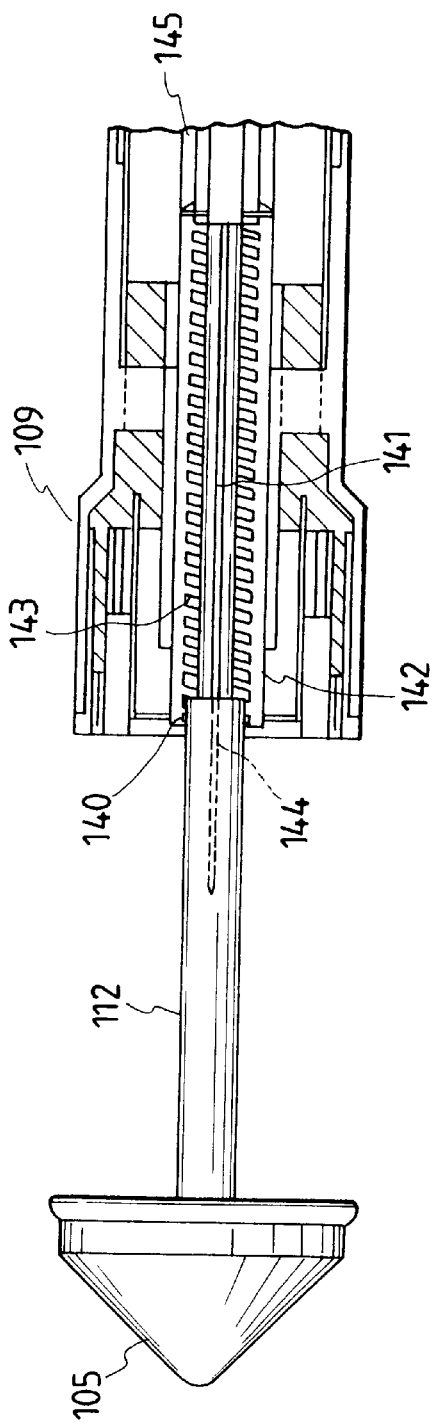
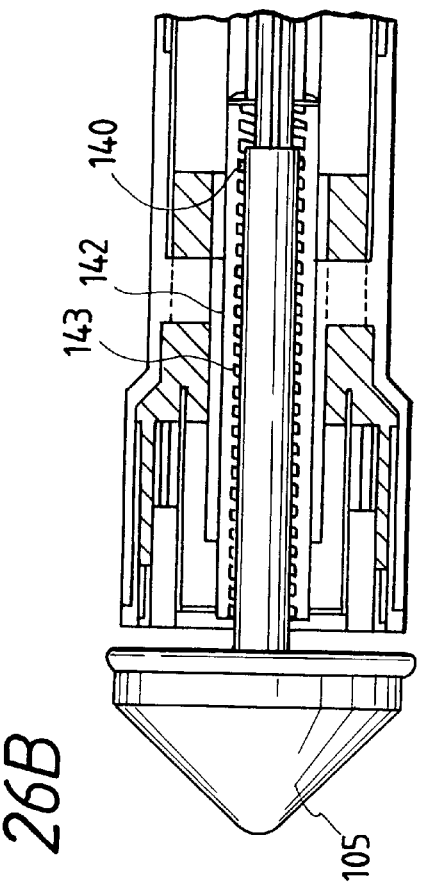
FIG. 26A
FIG. 26B

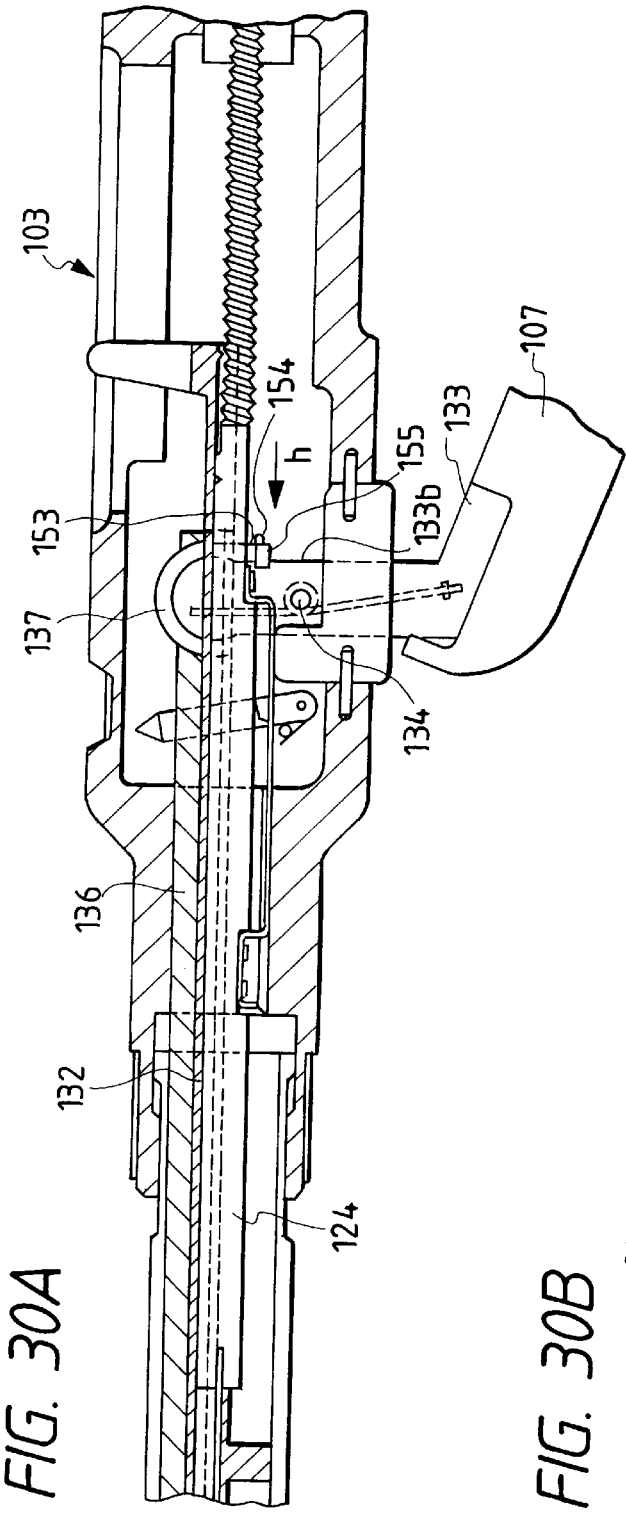
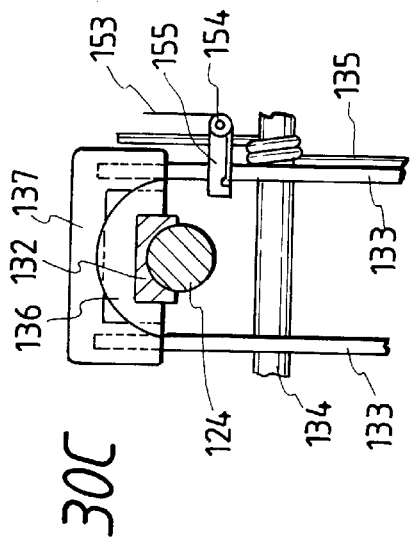
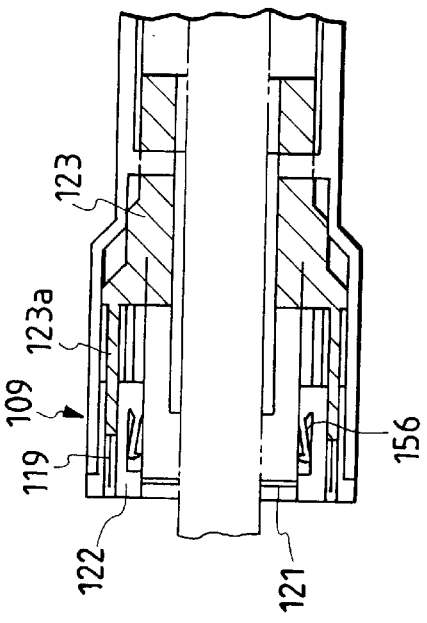
FIG. 30A
FIG. 30C
FIG. 30B

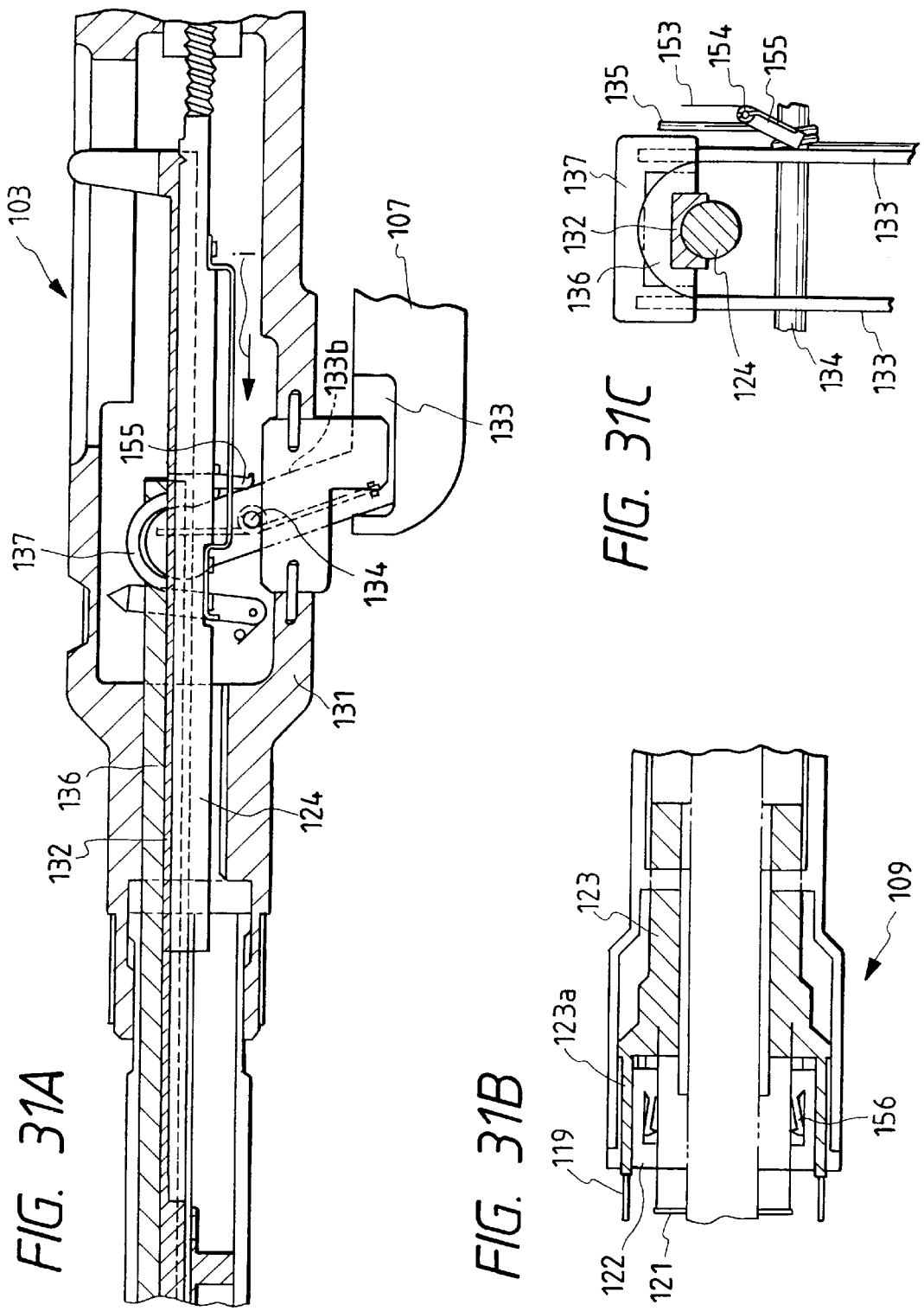

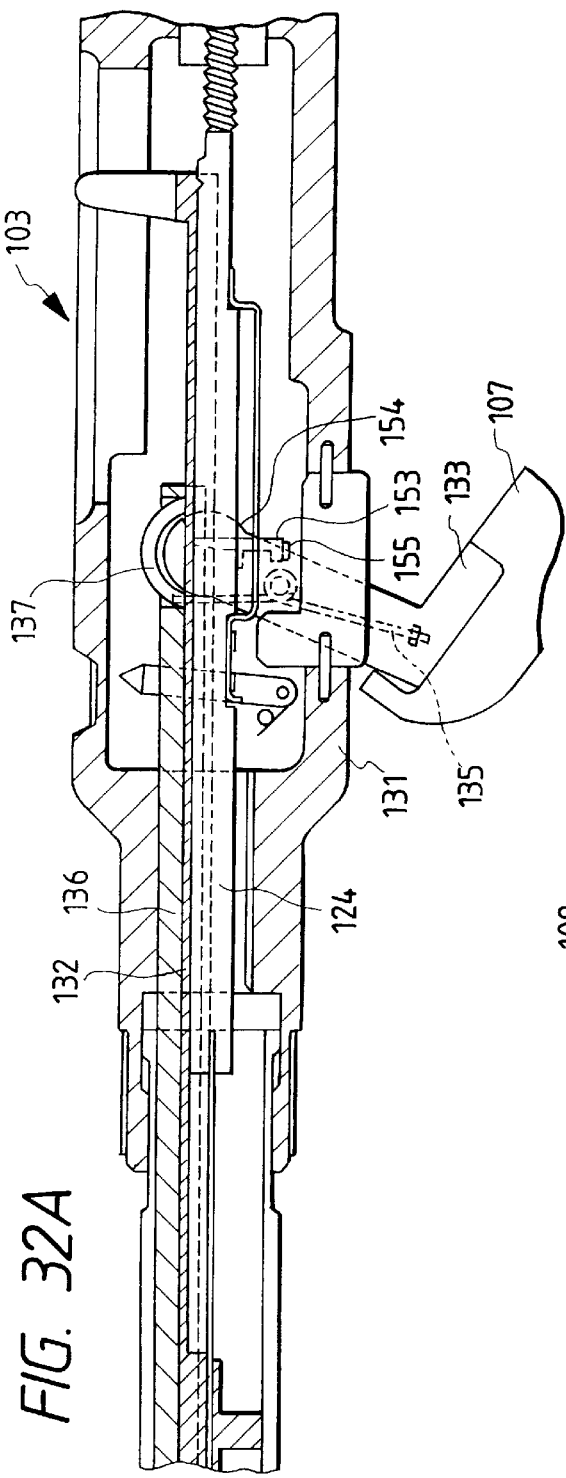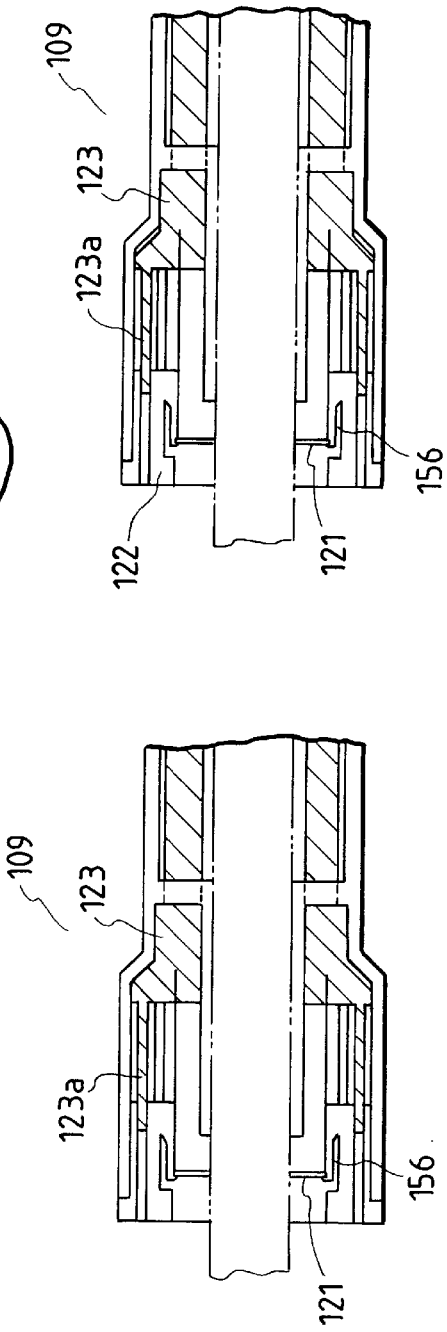
FIG. 32A
FIG. 32B
FIG. 32C

SURGICAL ANASTOMOSIS STAPLER

BACKGROUND OF THE INVENTION

1. Field of the Invention

The present invention relates to a medical suturing apparatus for use in surgical operations on tubular structures in the human body such as the intestine and esophagus.

2. Related Art

In the current practice of surgical operations on tubular structures such as intestine and esophagus, anastomosis is performed with a medical suturing apparatus comprising an operating member, an insertion member extending therefrom, a head disposed at the distal end of the insertion member which has a plurality of U-shaped staples arranged on the circumference, and an anvil disposed in a position opposed to the head for clinching the staples.

Commonly known suturing apparatus are operated as follows: the head and the anvil are inserted into two opposed tubular structures and, after the distance between the head and the anvil is shortened, the staples are expelled and clinched by slots in the opposite surface of the anvil while, at the same time, the excess tissue left inside of the staple line is severed by a cylindrical blade positioned inside of the staple line, whereupon the intended anastomosis is completed.

U.S. Pat. No. 5,392,979 discloses a suturing apparatus which permits the anvil to be attached to or detached from the head with comparative ease but in which the anvil is no longer detachable from the head if the distance between the two members has reached an optimal value for anastomosis. Then, a safety mechanism is released, whereupon it becomes possible to fire the staples. An indicator is used to provide a visual signal for the surgeon to know an optimal value of the head to anvil distance. A similar type of suturing apparatus is described in U.S. Pat. No. 5,205,459.

The suturing apparatus described in the two U.S. patents are of a disposable type, which is different from the device proposed in Unexamined Published Japanese Patent Application (kokai) No. 108347/1980. The latter type consists of an operating member, an insertion member, a staple cartridge and an anvil. The operating member combines with the insertion member to comprise a main body and the staple cartridge and the anvil which are disposed at the distal end of the insertion member are replaced after each surgical operation whereas the main body is usable more than once.

The suturing apparatus described above share the common structural feature that the legs of each staple disposed at the distal end of the insertion member are oriented distally so that they can be ejected in a distal direction.

A problem with the suturing apparatus disclosed in U.S. Pat. Nos. 5,392,979 and 5,205,459 is that even if the anvil is yet to be installed, the safety mechanism is released if the indicator signals an optimal distance for performing anastomosis and the surgeon may inadvertently fire staples, resulting in a waste of the staples or accidental ejecting of the circular blade. In addition, the suturing apparatus described in the two U.S. patents is of a disposable type and it must entirely be discarded after single use. Therefore, the apparatus must be purchased for each surgical operation and this only adds to the running cost of hospitals.

In contrast, the suturing apparatus disclosed in Unexamined Published Japanese Patent Application No. 108347/1980 permits repeated use of the main body by replacing the anvil and the staple cartridge. However, the anvil of this apparatus is of such a construction that it is threadably mounted to the rod at the distal end of the insertion member and, therefore, it is not ideal for handling in surgical operations where simple and quick procedures of replacement are necessary.

Further in addition, the known suturing apparatus for use in anastomotic surgical operations on tubular structures including the three devices described above share the common feature that the legs of staples are oriented distally and that therefore the surgeon cannot check immediately after his surgical operation as to whether the legs of the fired staples have been appropriately clinched; this has made it impossible to assure complete prevention of post-operative complications.

SUMMARY OF THE INVENTION

The present invention has been accomplished under these circumstances and has as an object providing a medical suturing apparatus that prevents unnecessary firing of staples, that permits simple replacements of the staple cartridge and the anvil head, that does not add to the running cost of medical institutions and that reduces the chance of the occurrence of post-operative complications.

Another object of the invention is to provide a medical suturing apparatus which, after the anvil has been installed at the distal end of the insertion member, prevents the anvil from being disconnected as the distance between the anvil and the head at the distal end of the insertion member is being adjusted and which also ensures that even if the lever of the operating member is gripped after staples have been fired, no troubles such as damage due to the inadvertent ejecting of the cylindrical cutter will occur.

The first object of the invention can be attained by a medical suturing apparatus including a main body that consists of an operating member and an insertion member extending therefrom and an anvil head that is disposed at the distal end of said main body for clinching a plurality of staples, characterized in that a staple head having an array of staples is disposed in a position opposed to the anvil head.

The suturing apparatus is used as follows in an anastomotic surgical operation. The staple head is inserted into an end of a severed section of the intestine and with a thin elongated linking portion of the staple head sticking out of the section, said one end of the intestine is purse-string sutured. The insertion member of the apparatus is inserted into either another incised area of the intestine or an opening of the patient and the other end of the severed section is purse-string sutured with the linking portion of the staple head at the distal end of the insertion member sticking out of said other end of the intestine.

After both ends of the intestine have been purse-string sutured, the staple head is installed on the linking portion at the distal end of the insertion member and the adjusting knob of the operating member is rotated to advance the staple head toward the anvil head. When the distance between the staple and the anvil head has reached an appropriate value for anastomosis, the lever of the operating member is gripped, whereupon the necessary force is transmitted through the linking portion of the staple head which connects to the distal end of the insertion member and staples are expelled from the staple head and their legs are clinched by means of the slots in the anvil head. At the same time, the excess tissue inside of the staple line is severed off with a cylindrical cutter.

The second object of the invention can be attained by a medical suturing apparatus including an operating member, an insertion member extending from said operating member, and an anvil head disposed at the head of said insertion member for clinching a plurality of staples, characterized in that said anvil head is detachable with respect to the head of the insertion member and that when said anvil head is installed on the head of the insertion member, the distance between said anvil head and said head of the insertion member can be fixed at desired value.

The suturing apparatus is used as follows in an anastomotic surgical operation. The anvil head is inserted into an end of a severed section of the intestine and said one end of the intestine is purse-string sutured around an anvil shaft from the anvil head which sticks out of the section. The insertion member of the apparatus is inserted into either another incised area of the intestine or an anal opening of the patient and the other end of the severed section is purse-string sutured with a trocar at the distal end of the insertion member sticking out of said other end of the section.

After both ends of the intestine have been purse-string sutured, the anvil shaft is installed on the head of the insertion member, with the trocar used as a guide, and the locking mechanism of the operating member is manipulated to ensure that the anvil head cannot be disconnected from the trocar. Thereafter, the adjusting knob of the operating member is rotated to move the anvil head toward the head of the insertion member. Having been already locked, the anvil head will not inadvertently be disconnected as it is moved toward the head of the insertion member.

When the distance between the anvil head and the head of the head of the insertion member has reached an optimal value for anastomosis, the safety lock is released and the lever of the operating member is gripped, whereupon staples are expelled toward the anvil head and clinched; at the same time, a cylindrical cutter severs off the excess tissue inside of the staple line to thereby complete the anastomotic operation. If desired, the anvil head can be disconnected from the head of the insertion member at any position in the process of moving the former toward the latter.

BRIEF DESCRIPTION OF THE DRAWINGS

FIG. 1A shows a general overall view of a medical suturing apparatus according to a first embodiment of the invention;

FIG. 1B is a side view of a staple head and an anvil head of the apparatus shown in FIG. 1A;

FIG. 2A is a longitudinal sectional side view of the staple head and the anvil head of the suturing apparatus according to the first embodiment of the invention, FIG. 2B is a cross section taken on line a—a of FIG. 1B, FIG. 2C is a cross section taken on line b—b of FIG. 1B, FIG. 2D is a side view of a staple;

FIGS. 4A and 4B show in perspective a staple head sleeve of the medical suturing apparatus according to the first embodiment of the invention;

FIG. 5A is a longitudinal sectional side view of the staple head and the anvil head, illustrating the operation of the medical suturing apparatus according to the first embodiment of the invention, FIG. 5B is a cross section taken on line c—c FIG. 5A;

FIG. 6A is a longitudinal sectional side view of the staple head and the anvil head, illustrating the operation of the medical suturing apparatus according to the first embodiment of the invention, FIG. 6B is a side view of a clinched staple;

FIG. 7 is a perspective exploded view of an insertion member of the medical suturing apparatus according to the first embodiment of the invention;

FIG. 14 is a longitudinal sectional side view of a staple head and an anvil head of a medical suturing apparatus according to a third embodiment of the invention;

FIG. 18A is a cross section of the suturing apparatus taken on line a—a of FIG. 17B, FIG. 18B is a cross section taken on line b—b of FIG. 17B, FIG. 18C is a longitudinal sectional side view of the head of an insertion member;

FIG. 19A is a longitudinal sectional side view of an operating member of the medical apparatus suturing according to the sixth embodiment of the invention, FIG. 19B is a cross section taken on line c—c of FIG. 19A;

FIG. 22 is a longitudinal sectional side view of the head of an insertion member and the operating member, illustrating another phase of the operation of the medical suturing apparatus according to the sixth embodiment of the invention;

FIG. 23 is a longitudinal sectional side view of the head of an insertion member and the operating member, illustrating still another phase of the operation of the medical suturing apparatus according to the sixth embodiment of the invention;

FIG. 25A is a longitudinal sectional side view of the head of an insertion member of a medical suturing apparatus according to a seventh embodiment of the invention, FIG. 25B is a cross section taken on line d—d of FIG. 25A, FIG. 25C is a cross section taken on line e—e of FIG. 25A;

FIG. 26A is a longitudinal sectional side view of the head of an insertion as it is connected to an anvil head, FIG. 26B is a longitudinal sectional side view of the anvil head as it has been moved to the head of an insertion member;

FIG. 30A is a longitudinal sectional side view of an operating member of a medical suturing apparatus according to a ninth embodiment of the invention, FIG. 30B is a longitudinal sectional side view of the head of an insertion member of the suturing apparatus, FIG. 30C is a sectional view taken by looking at FIG. 30A in the direction of arrow h;

FIG. 31A is a longitudinal sectional side view of the operating member of the medical suturing apparatus according to the ninth embodiment of the invention but in a different phase of its operation, FIG. 31B is a longitudinal sectional side view of the head of an insertion member of the suturing apparatus, FIG. 31C is a sectional view taken by looking at FIG. 31A in the direction of arrow i;

FIG. 32A is a longitudinal sectional side view of the operating member of the medical suturing apparatus according to the ninth embodiment of the invention but in yet another phase of its operation; and FIGS. 32B and 32C are longitudinal sectional side views of the head of an insertion member in two different states.

DETAILED DESCRIPTION OF THE INVENTION

Figure 3:
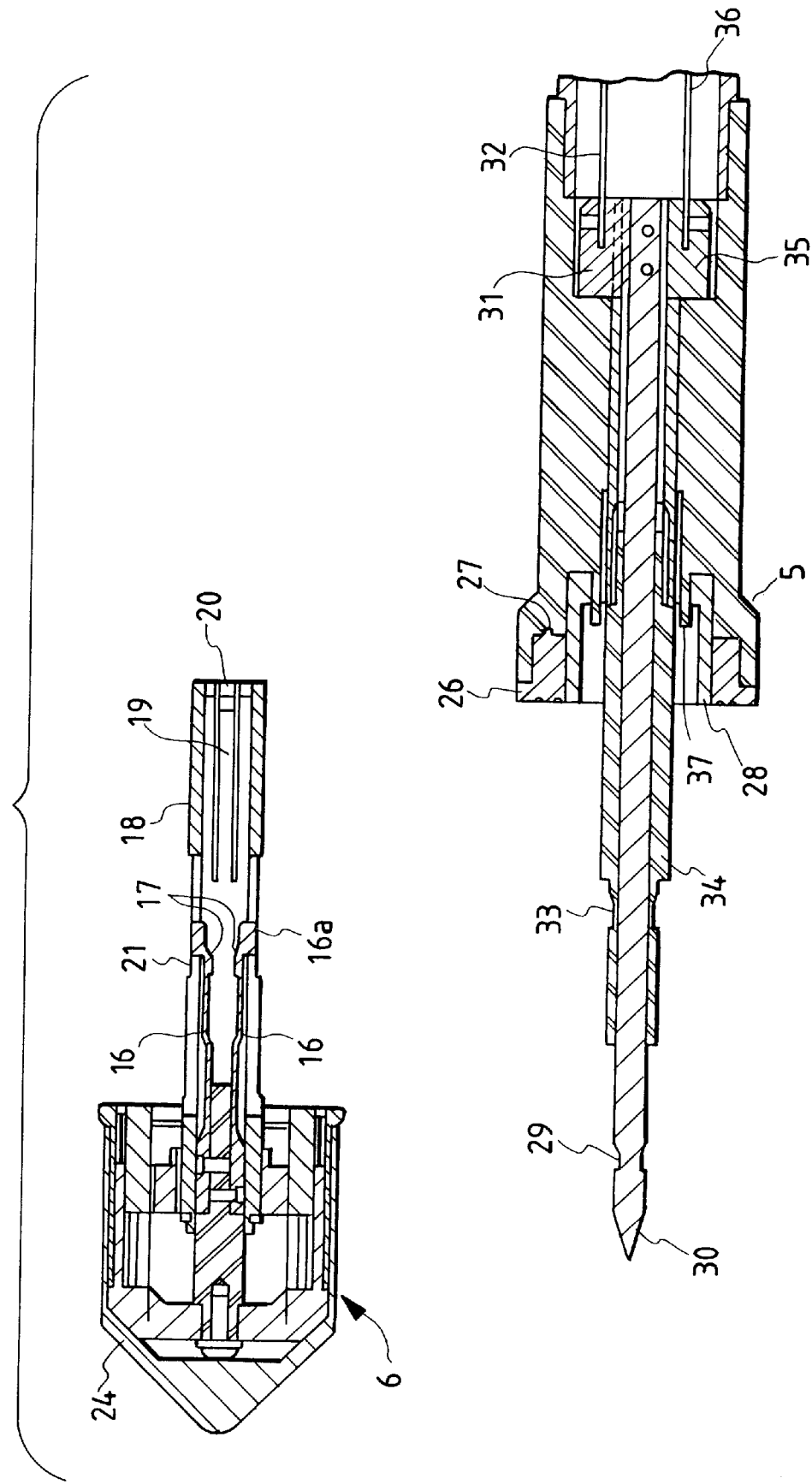
FIG. 3 is a longitudinal sectional side view of the staple head and the anvil head of the suturing apparatus according to the first embodiment of the invention.

Various embodiments of the present invention will now be described with reference to the accompanying drawings.

FIGS. 1 to 12 illustrate a first embodiment. As shown in FIG. 1A, a medical suturing apparatus generally indicated by 1 comprises a main body 2 which is composed of an operating member 3 and an insertion member 4 extending with a mild curvature from the operating member 3. Provided at the distal end of the insertion member 4 is an anvil head 5 which is to be described below more specifically. A staple head 6 which will also be described below more specifically is detachably provided on the anvil head 5.

The operating member 3 is fitted with an adjusting knob 7 which is rotated to retract the staple head 6 toward the anvil head 5, and a lever 8 which is gripped to have staples 11 (see below) expelled as a tissue binding fastener from the staple head 6.

The staple head 6 and the distal end of the insertion member 4 have the structural features which are described below with reference to FIGS. 2 to 5. As shown in FIG. 2D, each staple 11 is U-shaped and consists of a base 11a and two legs 11b which are generally perpendicular to the base 11a.

As shown in FIGS. 2A and 2B, the staple head 6 is fitted in a position opposed to the anvil head 5 which is provided at the distal end of the insertion member 4 and the staple head 6 normally contains a plurality of staples 11 in an annular array of recessed staple channels 12. The staples 11 in the staple channels are oriented in such a way that the tips of the two legs 11b extending from the bases 11a are directed toward the anvil head 5. Provided inward of the staple channels 12 is a cylindrical cutter 13 that is coaxial with the channels and which will cut off a tissue section. The cutter 13 has a sharp blade 13a directed toward the anvil head 5 and it is fitted on a staple pusher 14 which expels staples 11 by directly pushing them out.

The anvil head side of the staple pusher 14 is provided with a plurality of rod-shaped projections 14a which are partially inserted into the respective staple channels 12. A staple drive shaft 15 for driving the staple pusher 14 is fixed through axial the center of the staple pusher 14.

The anvil head side of the staple drive shaft 15 is fitted with a pair of leaf springs 16 and the distal end of each leaf spring which is on the anvil head side is provided with an inwardly projecting latch 17. The anvil head side of the staple head 6 is provided with a staple head sleeve 18 for accommodating the staple drive shaft 15 and the leaf springs 16.

As shown in FIGS. 3 and 4, a pair of leaf springs 19 are molded on the anvil head side of the staple head sleeve 18. The distal end of each leaf spring 19 is provided with an inwardly projecting latch 20. Leaf spring guiding slots 18a are provided on the outer circumference of the staple head sleeve 18 for permitting the heads of leaf springs 16a to become flared to come outside of the outer circumference of the staple head sleeve 18. The leaf spring guiding slots 18a are sized to be longer than the axial length of the leaf spring heads 16a. As shown in FIGS. 1B and FIG. 4A, a plurality of ribs 21 are provided on the outer circumference of the anvil head side of the staple head sleeve 18 as means of positioning it in the radial direction of staples 11.

Further, as shown in FIG. 2B, a staple channel casing 12a forming the staple channels 12 has a keyway 22 which is positioned by a rib 23 formed distally on the staple head sleeve 18. This allows the positioning of the staple head sleeve 18 with respect to the radial direction of staples 11. The individual parts to be accommodated within the staple head 6 are retained by a staple head casing 24.

As shown in FIG. 2C, the anvil head 5 at the distal end of the insertion member 4 is provided with an anvil 26 which has an annular array of slots 25 for clinching staples 11. Means 27 is also provided to position the slots 25 in a radial direction. A plate 28 for receiving the cylindrical cutter 13 is provided coaxially with the anvil 26 and in a position opposed to the cutter 13, and a trocar 30 is provided inward of and through the center of the receiving plate 28.

The trocar 30 is provided with circular grooves 29 which engage the latches 17 at the distal end of the leaf springs 16 fitted on the staple drive shaft 15. The trocar 30 is coupled to a trocar drive guide 31 on the actuator side and a trocar drive member 32 is provided to ensure that the force produced by gripping the lever 8 of the actuator 3 is transmitted to the trocar drive guide 31. Provided exterior to the trocar 30 is a trocar sleeve 34 that accommodates the trocar 30 and which has circular grooves 33 that engage the latches 20 at the distal end of the leaf springs 19 fitted on the staple head sleeve 18.

As shown in FIG. 3, the trocar sleeve 34 is coupled on the actuator side to a staple head drive guide 35 and a tension member 36 is also provided for ensuring that the force produced by rotating the adjusting knob 7 of the actuator 3 is transmitted to the staple head drive guide 35. The trocar drive guide 31 and the staple head drive guide 35 perform such a function within the insertion member 4 that a positional relationship in which the trocar drive member 32 is not coaxial with the tension member 36 is transformed to a relationship in which the trocar 30 is coaxial with the trocar sleeve 34. The trocar sleeve 34 is accommodated in the anvil head 5, which is internally provided with a plurality of keyways 37 for positioning the staple head 6 in a radial direction.

Having described above the construction of the medical suturing apparatus according to the first embodiment of the invention, we now describe how it is operated.

First, the staple head 6 is inserted into an end of a tissue section of a tubular structure, say, intestine and said one end is purse-string sutured around the staple head sleeve 18. In addition, the insertion member 4 is inserted into the other end of the tissue section and said other end is also purse-string sutured around the trocar sleeve 34.

Thereafter, the trocar 30 and the trocar sleeve 34 are inserted into the staple head sleeve 18 of the staple head 6, whereupon the heads of leaf springs 16a will flare to come outside of the leaf spring guiding slots 18a, causing the staple head 6 to be installed at the distal end of the insertion member 4. In this case, the circular grooves 29 at the distal end of the trocar 30 and the circular grooves 33 on the trocar sleeve 34 are in engagement with the latches 17 and 20, respectively (see FIG. 2A).

When the adjusting knob 7 of the operating member 3 is rotated, a tension is transmitted through the staple head drive member 36, staple head drive guide 35 and trocar sleeve 34 to reach the staple head sleeve 18, causing the staple head 6 to be retracted toward the anvil head 5 (see FIG. 5A).

When the staple head 6 has been retracted to a certain extent, the ribs 21 on the staple head sleeve 18 come into engagement with the keyways 37 on the inner surface of the anvil head 5, whereby the radial positioning of the staple head 6 is completed automatically. FIG. 5B shows how the ribs 21 engage the keyways 37 on the anvil head 5 and how the leaf spring heads 16a contact ridges 37a between adjacent keyways 37.

If the indicator (not shown) signals the surgeon that the distance between anvil 26 and staple head 6 has attained an optimal value for performing anastomosis, the surgeon releases the safety lock (not shown). If he grips the lever 8, the tension is transmitted through the trocar drive member 32, trocar drive guide 31, trocar 30, leaf springs 16 and staple drive shaft 15 to reach the staple pusher 14, which then causes staples 11 to be ejected from the staple channels 12 as shown in FIG. 6A. The ejected staples 11 are clinched by the slots 25 in the anvil 26. FIG. 6B shows a clinched staple 11. Under the tension transmitted from the operating member 3, the leaf spring heads 16a tend to flare outwardly but, in fact, the ridges 37a between adjacent keyways 37 prevent those heads from flaring but, instead, they will be moved toward the actuator 3 along the leaf spring guiding slots 18a, thereby restricting the action of the staple pusher 14 such that it will not move toward the operating member 3 by a more-than-necessary amount (see FIG. 4B). At the same time, the cylindrical cutter 13 is pushed out of the staple head 6 to sever the excess tissue of the intestine inside of the staple line, whereby the anastomotic operation is completed.

We next describe the proximal side of the operating member 3 and the insertion member 4 by referring to FIGS. 7 to 12. As shown in FIG. 7 which is an exploded view of the insertion member 4, the interior of the proximal side of the insertion member 4 comprises the staple head drive member 36 and the trocar drive member 32 which are contained in a curved insertion shaft 46, with the member 32 being held between guide members 45a and 45b and the member 36 held between guide members 45b and 45c, such that the member 32 is axially movable between the guide members 45a and 45b whereas the member 36 is axially movable between the guide members 45b and 45c, with the radial relative positions of the two members 32 and 36 being invariable throughout the insertion shaft 46. The trocar drive member 32 is pierced at the proximal end to make a hole 32a.

Figure 8:
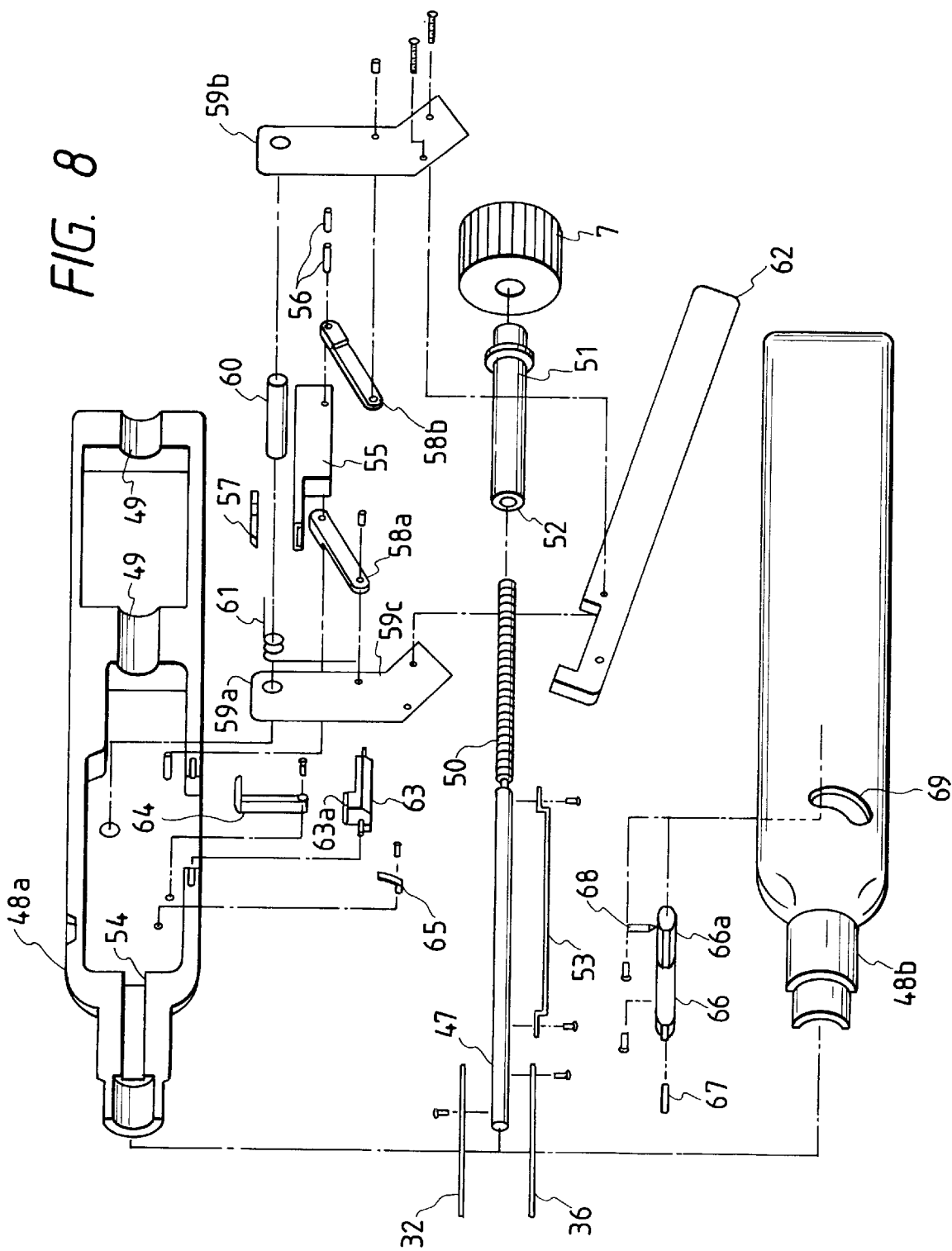
FIG. 8 is a perspective exploded view of an operating member of the medical suturing apparatus according to the first embodiment of the invention.
Figure 9:
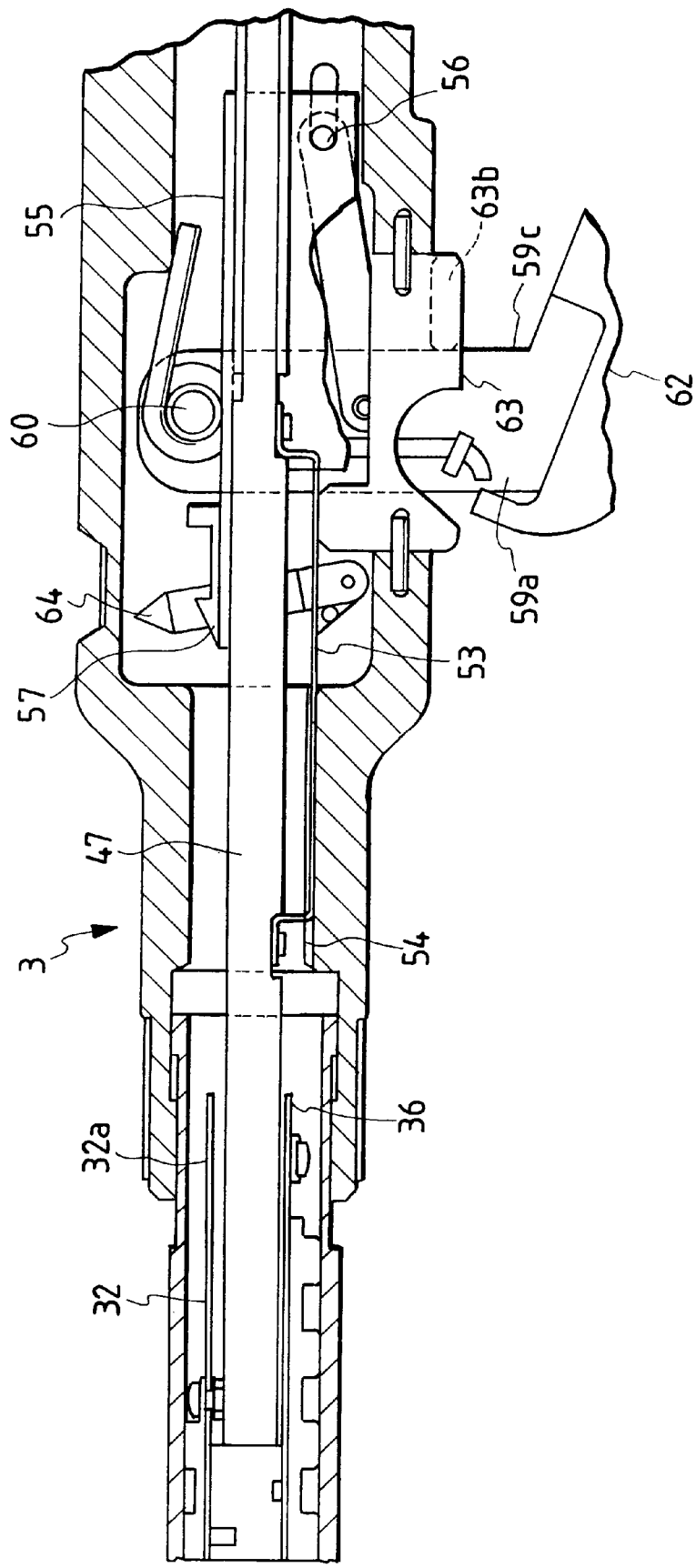
FIG. 9 is a longitudinal sectional side view of the operating member, illustrating a phase of the operation of the medical suturing apparatus according to the first embodiment of the invention.
Figure 10:
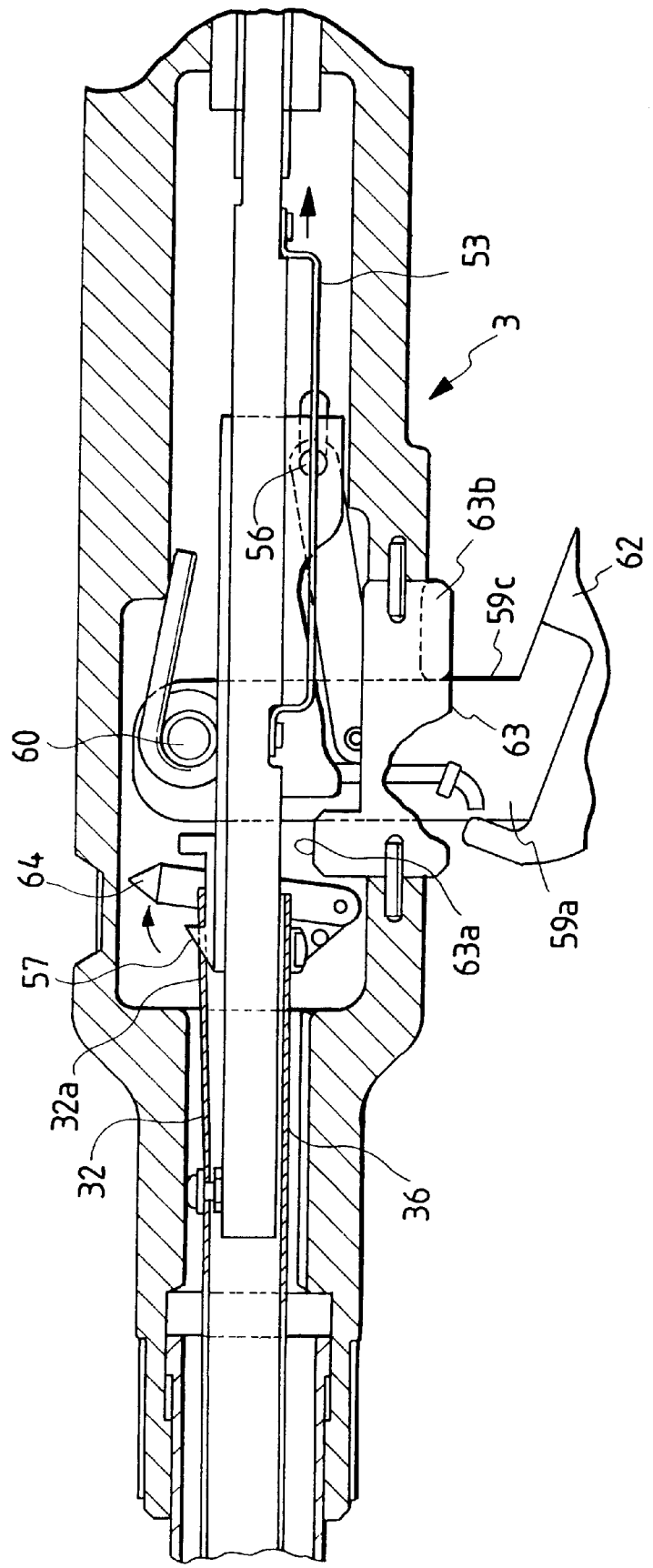
FIG. 10 is a longitudinal sectional side view of the operating member, illustrating another phase of the operation of the medical suturing apparatus according to the first embodiment of the invention.

As shown in FIG. 8, the operating member 3 contains a rod 47 which extends through the axial center to fit in semicircular grooves 49 provided in two casings 48a and 48b which compose the operating member 3. The proximal side of the rod 47 has a portion provided with an angular external thread 50 and this portion is threaded into an angular screw shaft 51 provided with an angular internal thread 52. The rotatable adjusting knob 7 is provided at the proximal end of the angular screw shaft 51.

A sheet-like safety guide 53 is mounted to the rod 47. The safety guide 53 engages a rectangular groove 54 provided near the distal end of the casing 48a. The trocar drive member 32 is mounted at the distal end of the rod 47 in such a way that it is slidable relation to the rod 47. The staple head drive member 36 is also mounted to the rod 47. The insertion shaft 46 is mounted in such a way that it is held between two casings 48a and 48b.

A U-shaped staple actuating member 55 is slidably disposed within the casing 48 such that it surrounds the rod 47. A latch 57 is fixed to the top surface of the staple actuating member 55. Arms 58a and 58b are mounted to opposite lateral sides of the staple actuating member 55 by means of pins 56. The arms 58a and 58b are rotatably mounted to triggers 59a and 59b, respectively. Triggers 59a and 59b are mounted such that they are free to rotate-about a thick pin 60 mounted to the casing 48. A coil spring 61 is passed through the thick pin 60 and an end of it is fixed to the trigger 59a. The triggers 59a and 59b are fixed in such a way that a lever 62 is held therebetween.

Underneath the safety guide 53 is provided a safety lock 63 which is mounted to the casings 48a and 48b in an axially rotatable manner such that its top surface 63a will contact the underside of the safety guide 53, with the locking portion 63b being in contact with the edge 59c at the proximal end of the trigger 59a. An indicator 64 is rotatably mounted to the inner lateral side of the casing 48b in such a way that it is distally urged by means of a J-shaped leaf springs 65. A release lever 66 has a pin 67 at an end and a tension spring 68 at the other end. The release lever 66 is rotatably mounted to the casing 48b, with a finger grip 66a sticking out of it through a slot 69 made in it. The slot 69 is of such a shape as to enable the actuating of the finger grip 66a.

We now describe the operation of the suturing apparatus according to the first embodiment of the invention. First consider the initial state shown in FIG. 9. When the adjusting knob 7 of the operating member 3 is rotated clockwise, the rod 47 is actuated by the angular thread to be retracted toward the adjusting knob 7 (or the operator), whereupon a tension is exerted on the staple head drive member 36 fitted to the distal end of the rod 47 and transmitted through the staple head drive guide 35 to reach the trocar sleeve 34 such that the staple head 6 installed on the trocar sleeve 34 is moved to a retracted position.

In this process, a moment is exerted on the rod 47; however, the rod will not rotate since the safety guide 53 is slidably mounted to the rectangular groove 54 which serves to prevent the rotation of the rod 47. In addition, even at a time just before the staple head 6 is fully retracted toward the operator, the safety guide 53 will get into the U-shaped staple actuating member 55 to thereby prevent the rod 47 from rotating.

When the indicator 64 gives the surgeon a visual signal indicating that the distance between the staple head 6 and the anvil 26 has reached an optimal value, the safety guide 53 in the casing 48 is disengaged from the top surface 63a of the safety lock 63. In addition, the trocar drive member 32 slidably fitted to the distal end of the rod 47 is also retracted to the operator, causing the latch 57 to come into engagement with the hole 32a made at the proximal end of the trocar drive member 32 (see FIG. 10).

Then, the safety lock 63 is rotated about an axis parallel to the axis of the rod 47, whereupon the locking portion 63b which has been in contact with the edge 59c at the proximal end of the trigger 59a is disengaged from it, causing the triggers 59a and 59b to become freely rotatable. If the surgeon grips the lever 62, the triggers 59a and 59b will rotate about the thick pin 60, so that the arms 58a and 58b which are rotatably fitted to the triggers 59a and 59b, respectively, are pushed toward the proximal end, thereby causing the staple actuating member 55 to be retracted toward the proximal end via elongated pins 56.

Figure 11:
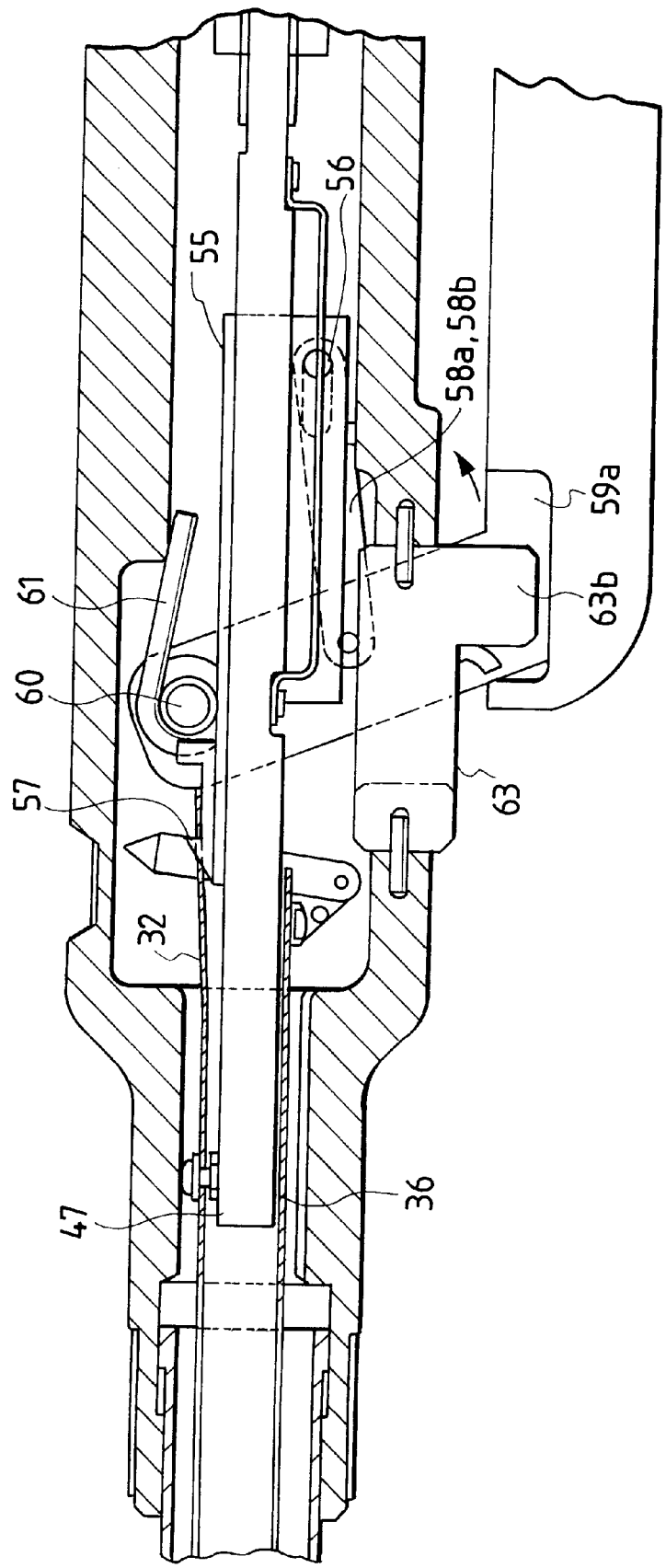
FIG. 11 is a longitudinal sectional side view of the operating member, illustrating still another phase of the operation of the medical suturing apparatus according to the first embodiment of the invention.

In this process, a tension is also exerted on the trocar drive member 32 which is in engagement with the latch 57 on top of the staple actuating member 55, causing the trocar 30 at the distal end of the insertion member 4 to be moved to the retracted position via the trocar drive guide 31; as a result, staples 11 are fired from within the staple head 6 (see FIG. 11).

After the firing of the staples 11, the lever 62 is released, whereupon the triggers 59a and 59b return to their initial position by the action of the coil spring 61 and a compressive force is transmitted through arms 59a/58b, staple actuating member 55, latch 57 and trocar drive member 32 to reach the trocar 30 such that the rod-shaped projections 14a of the staple pusher 14 are eventually retracted into the staple channels 12. In this case, the leaf springs 19 in the staple head sleeve 18 are in contact with the inner surface of the anvil head 5 so they will not flare but prevent the staple head 6 from being disconnected from the anvil head 5.

Figure 12:
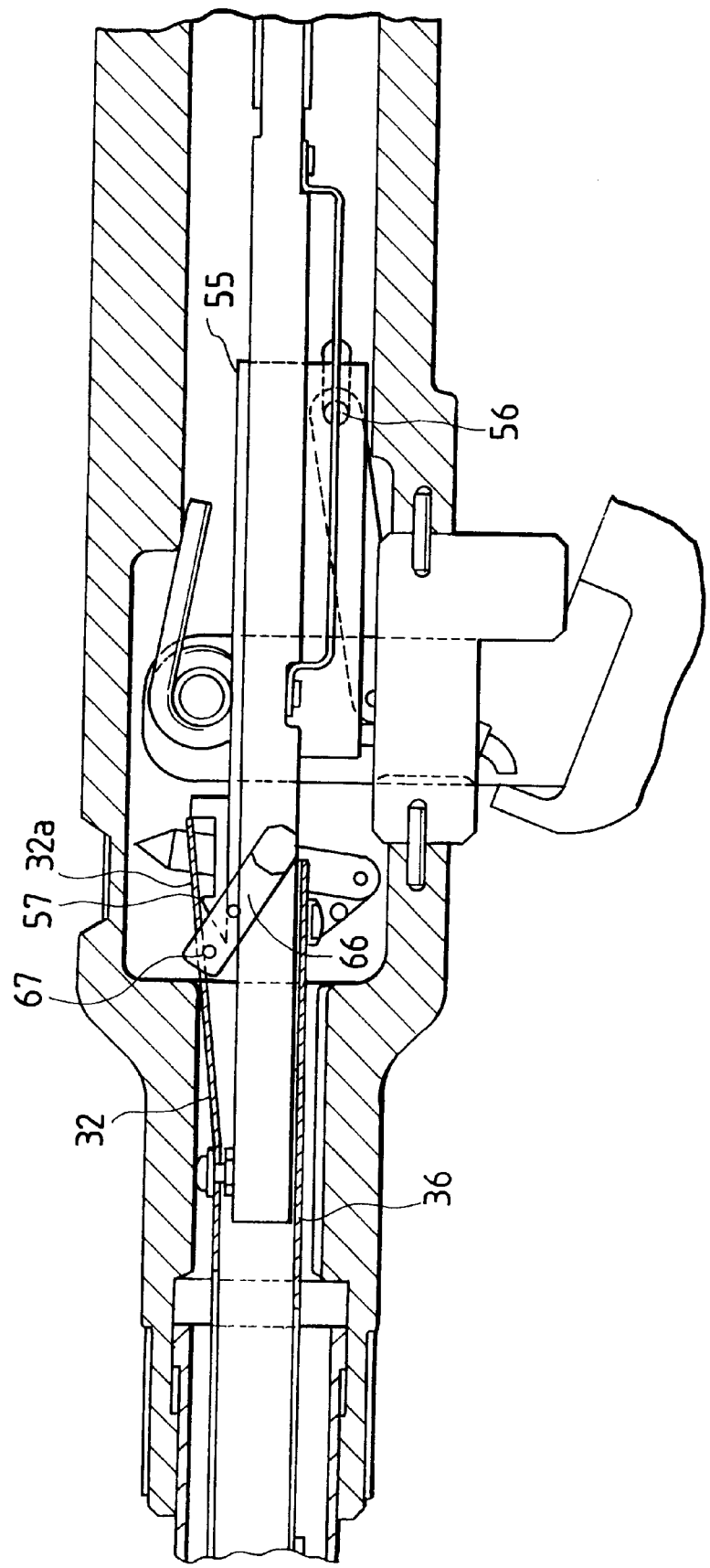
FIG. 12 is a longitudinal sectional side view of the operating member, illustrating yet another phase of the operation of the medical suturing apparatus according to the first embodiment of the invention.

After the firing of the staples 11, the distance between the staple head 6 and the anvil head 26 is increased by lowering release lever 66 on the casing 48b of the operating member as shown in FIG. 12. The pin 67 on the release lever 66 will then contact the trocar drive member 32 to raise it, whereupon the hole 32a in the trocar drive member 32 comes out of engagement with the latch 57 on the staple actuating member 55. If the adjusting knob 7 is rotated counterclockwise, a compressive force is exerted on the staple head drive member 36 and the trocar sleeve 34 is pushed distally via the staple head drive guide 35, whereupon the staple head 6 is moved distally away from the anvil head 5.

After the hole 32a in the trocar drive member 32 has come out of engagement with the latch 57 to eventually cause the distal movement of the staple head 6, the surgeon may remove the finger from the finger grip 66a of the release lever 66 so as to bring it into the initial position.

In order to withdraw the medical suturing apparatus 1 from a tubular structure such as a section of the intestine, the release lever 66 of the operating member 3 may be lowered, whereupon the trocar drive member 32 is disengaged from the latch 57; if the adjusting knob 7 is then rotated counterclockwise (by about 120 degrees), the staple head 6 will depart from the anvil head 5. If the lever 8 is gripped with force in this condition, neither the rod-shaped projections 14a of the staple pusher 14 nor the cylindrical cutter 13 will project beyond the staple head 6. Subsequently, the insertion member 4 is rotated to be withdrawn from the section of the intestine. The staple head 6 of the used medical suturing apparatus 1 is removed from the trocar sleeve 34 and a new staple head 6 is replaced to enable repeated use of the main body 2.

Thus, the staple head 6 is incapable of firing staples 11 or ejecting the cylindrical cutter 13 on its own. Staples can only be fired after the passage of the following three stages: installing the staple head 6 at the distal end of the insertion member 4; adjusting the distance between the staple head 6 and the anvil head 5; and releasing the safety lock 63. Compared to the conventional medical suturing apparatus, the apparatus of the invention has the advantage that even if assistants to the surgeon forget to equip the suturing apparatus with the anvil head, unnecessary firing of staples can be precluded and the adverse effect of the cylindrical cutter can be prevented to thereby ensure utmost safety until an anastomotic operation is completed.

The conventional suturing apparatus have had another problem in that once the safety lock has been released, the gripping of the lever of the used apparatus will cause the staple pusher or the cylindrical cutter to be ejected no matter where the anvil head is positioned. This is not the case with the medical suturing apparatus of the first embodiment of the invention; even if the surgeon inadvertently grips the lever 62 with the safety lock 63 having been released after the firing of staples in the surgical operation, neither the rod-shaped projections 14a of the staple pusher 14 nor the cylindrical cutter 13 will be ejected from the staple head 6 unless the distance between the anvil surface 26 and the staple head 6 has reached an appropriate value for firing staples 11; this offers the advantage of securing great safety after the anastomotic operation.

Another advantage of the suturing apparatus of the invention is that the staple 11 in the staple head 6 have the legs 11b oriented toward the anal opening of the patient (i.e., toward the operator); therefore, after a sequence of steps in the anastomotic operation, the surgeon may insert an endoscope into the anal opening of the patient in order to check if the legs 11b of the fired staples 11 have been properly clinched. Thus, the occurrence of post-operative complications can be minimized.

Yet another advantage of the suturing apparatus of the invention is that it permits repeated use of the main body 2 since the spent staple head 6 can be disconnected form the distal end of the insertion member 4 and a new staple head 6 may simply be replaced. Hence, compared to the disposable type, the suturing apparatus of the invention which can be used many times will not add to the running cost of medical institutions. Further in addition, the cylindrical cutter 13 which is accommodated within the staple head 6 can be replaced with a new cutter concurrently with the replacement of the staple head; therefore, high cutting performance will be maintained for an indefinite period.

Figure 13A:
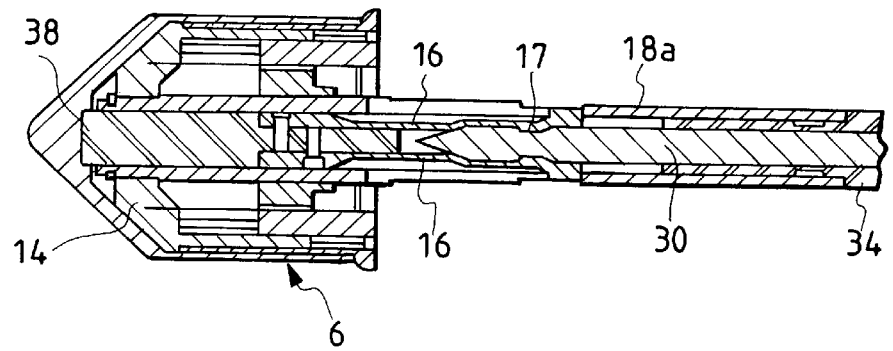
FIG. 13A is a longitudinal sectional side view of a staple head of a medical suturing apparatus according to a second embodiment of the invention, from which staples are yet to be fired.
Figure 13B:
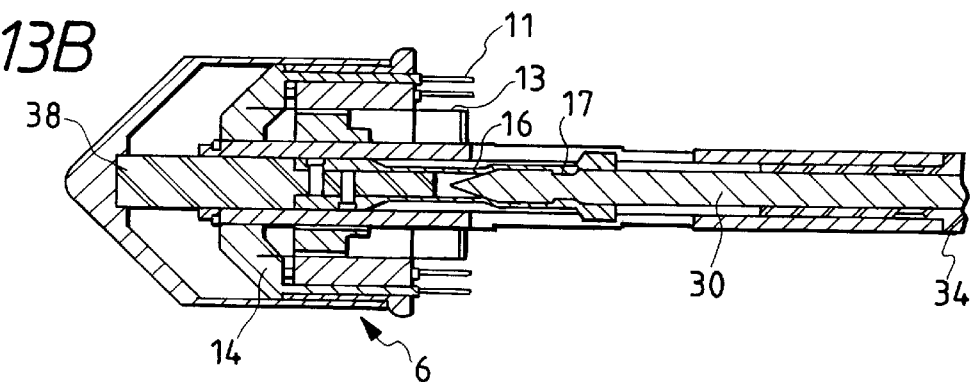
FIG. 13B is a longitudinal sectional side view of the staple head, from which staples have been fired.

FIG. 13 shows a second embodiment of the invention and the structural parts which are identical to those employed in the first embodiment are identified by like numerals and will not be described in detail. The second embodiment is essentially the same as the first embodiment except for the following: the staple head sleeve 18 is replaced by a staple head sleeve 18a; the staple drive shaft 15 is replaced by a staple head shaft 38; the trocar 30 is coupled to the staple head drive member 36; and the trocar sleeve 34 is coupled to the trocar drive member 32.

The staple head sleeve 18a in the second embodiment is fitted to the staple pusher 14 and the staple head shaft 38 supports the staple head 6. The trocar 30 at the distal end of the insertion member 4 is connected to the adjusting knob 7 of the operating member 3 via the staple head drive member 36 in the insertion shaft 46 and the trocar sleeve 34 is so adapted that the force produced by gripping the lever 8 is transmitted through the trocar drive member 32 in the insertion shaft 46.

The staple head sleeve 18a is designed to be mountable to the trocar sleeve 34 at the distal end of the insertion member 4 and the leaf springs 16 fitted on the staple head shaft 38 are designed to be mountable on the trocar 30 by means of latches 17.

Having these structural features, the medical suturing apparatus of the second embodiment is used as follows. To begin with, as in the first embodiment, two ends of a section of the intestine are purse-string sutured around the staple head sleeve 18a and the trocar sleeve 34. If the staple head 6 is installed on the trocar 30 at the distal end of the insertion member 4, the staple head sleeve 18a is mounted on the trocar sleeve 34 whereas the leaf springs 16 fitted in the staple head shaft 38 are mounted to the trocar 30.

When the adjusting knob 7 of the operating member 3 is rotated, a tension is transmitted to the trocar 30 through the staple head drive member 36; the tension is further transmitted through the leaf springs 16 and staple head shaft 38 to reach the staple head 6, whereupon said staple head 6 is moved toward the anvil head 5.

When the relative positions of the staple head 6 and the anvil 26 have attained an optimal relationship, the surgeon grips the lever 8 of the operating member 3, whereupon the tension is transmitted through the trocar drive member 32, trocar sleeve 34 and the staple head sleeve 18a to reach the staple pusher 14, which then causes staples 11 to be ejected from the staple channels 12. The ejected staples 11 are clinched by the slots 25 in the anvil 26. At the same time, the cylindrical cutter 13 is pushed out of the staple head 6 to sever the excess tissue of the intestine inside the staple line, whereby the anastomotic operation is completed.

Thus, the second embodiment produces the same result as the first embodiment.

FIG. 14 shows a third embodiment of the invention and the structural parts which are identical to those employed in the first embodiment are identified by like numerals and will not be described in detail. The third embodiment is essentially the same as the first embodiment except for the following: the staple head assembly 6 consists of two staple heads 6a and 6b having different outside diameters; the anvil head assembly 5 of the main body 2 is so adapted that two anvils 26a and 26b of different outside diameters and two receiving plates 28a and 28b of different outside diameters can selectively be mounted to and dismounted from the anvil head assembly 5. It should be noted that the anvils 26a and 26b are mounted to the receiving plates 28a and 28b, respectively, so that they can be mounted to and dismounted from the anvil head assembly as a single anvil set 39a or 39b. In order to prevent wrong combinations, the staple head 6a and anvil set 39a which have a first outside diameter combination are desirably baled together, and so are the staple head 6b and anvil set 39b which have a second outside diameter combination.

The third embodiment offers the following advantage: even if the outside diameter of a first selected staple head 6a does not fit the inside diameter of a section of the intestine to which anastomosis is to be applied, the main body 2 need not be simply discarded but it may still be used after replacing the staple head 6a with a second staple head 6b of a different outside diameter which accommodates staples 11. At the same time, the anvil set 39b consisting of the anvil 26b which is mounted to the receiving plate 28b and baled together with it may be placed in registry using the positioning means 27 such that the anvil set 39b can be replaced on the anvil head 5 of the main body 2.

According to the third embodiment of the invention, the advantages of the first embodiment are of course attained. In addition, it provides a particular advantage over the disposable type of anastomotic suturing device which has to be totally discarded even if one finds that the staple head or anvil head in an unpacked bale does not have an outside diameter that fits the inside diameter of a section of a tubular structure such as the intestine; the advantage of the suturing apparatus according to the third embodiment is such that even in this situation, the main body 2 can still be used by replacing the staple head 6a with staple head 6b of a different size or vice versa. Further in addition, the main body 2 can repeatedly be used by replacing the spent staple head 6a with a new staple head 6b or vice versa. Because of these advantages, a substantial cost reduction can be realized in hospitals as compared to the use of disposable suturing apparatus.

Figure 15A:
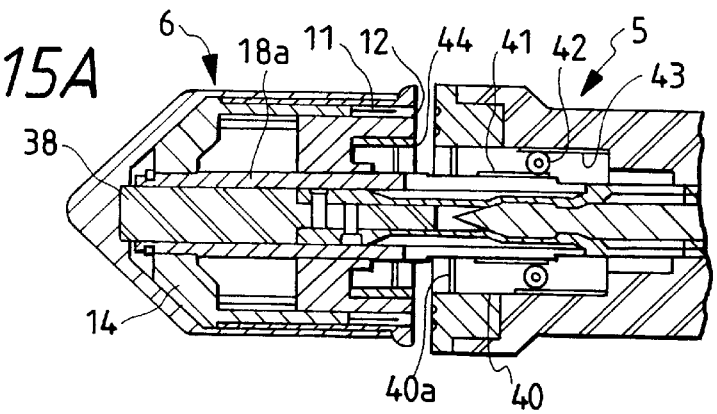
FIG. 15A is a longitudinal sectional side view of a staple head and an anvil head of a medical suturing apparatus according to a fourth embodiment of the invention, from which staples are yet to be fired.

FIG. 15 shows a fourth embodiment of the invention and the structural parts which are identical to those employed in the first and second embodiments are identified by like numerals and will not be described in detail. The fourth embodiment is essentially the same as the first and second embodiments except for the following: the cylindrical cutter 13 is replaced by a cylindrical cutter 40 which is placed within the anvil head 5, with its sharp blade 40a directed toward the staple head 6; the cylindrical cutter 40 is actuated by drive means which consists of racks 41 on the outer circumference of the staple head sleeve 18a, racks 43 on the inner side of the cylindrical cutter 40, and pinions 42 meshing with the racks 41 and 43; and receiving plates 44 are disposed within the staple head 6 which is in a face-to-face relationship with the cylindrical cutter 40.

Having these structural features, the medical suturing apparatus of the fourth embodiment is used as follows. To begin with, as in the first and second embodiments, two ends of a section of the intestine are purse-string sutured around the staple head sleeve 18a and the trocar sleeve 34. If the staple head 6 is fitted to the trocar 30 at the distal end of the insertion member 4, the staple head sleeve 18a is mounted to the trocar sleeve 34 whereas the leaf springs 16 fitted in the staple head shaft 38 are mounted to the trocar 30. When the adjusting knob 7 of the operating member 3 is rotated, a tension transmitted to the trocar 30 is further transmitted to the leaf springs 16 and the staple head 6, which is then moved toward the anvil 26 (see FIG. 15A).

When the relative positions of the staple head 6 and the anvil 26 have attained an optional relationship, the surgeon grips the lever 8 of the operating member 3, whereupon the tensions transmitted through the trocar sleeve 34 and the staple head sleeve 18a to reach the staple pusher 14, which then causes staple 11 to be ejected from the staple channels 12.

The ejected staples 11 are clinched by the slots 25 in the anvil 26. At the same time, the staple head sleeve 18a is retracted toward the anvil head 5, whereupon the racks 41 move the racks 43 toward the staple head 6 via pinions 42, causing the sharp blade 40a of the cylindrical cutter 40 to project from the anvil head 5.

Figure 15B:
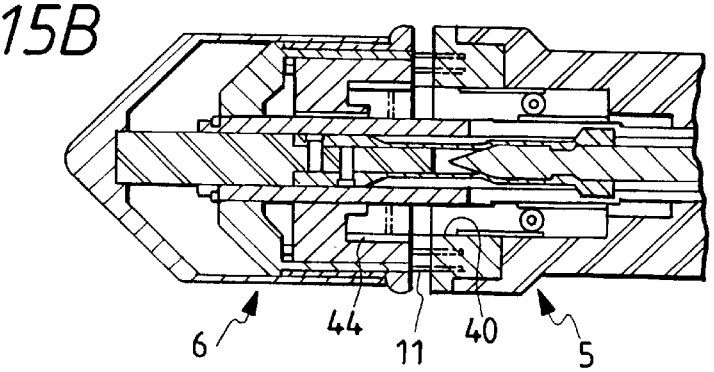
FIG. 15B is a longitudinal sectional side view of the staple head and the anvil head of the apparatus, from which staples have been fired.

Then, the cylindrical cutter 40 is urged against the receiving plate 44 in the staple head 6 to sever the excess tissue of the intestine inside the staple line, whereby the anastomotic operation is completed (see FIG. 15B). After the end of the surgical operation, the staple head 6 is discarded and the main body 2 is fitted with a new staple head 6 for subsequent use.

According to the fourth embodiment, the advantages of the second embodiment are attained and, in addition, the disposing of the cylindrical cutter 40 within the anvil head of the main body 2 contributes to reduce the cost of replacement of staple head 6 and this results in a saving of the cost of each surgical operation.

Figure 16A:
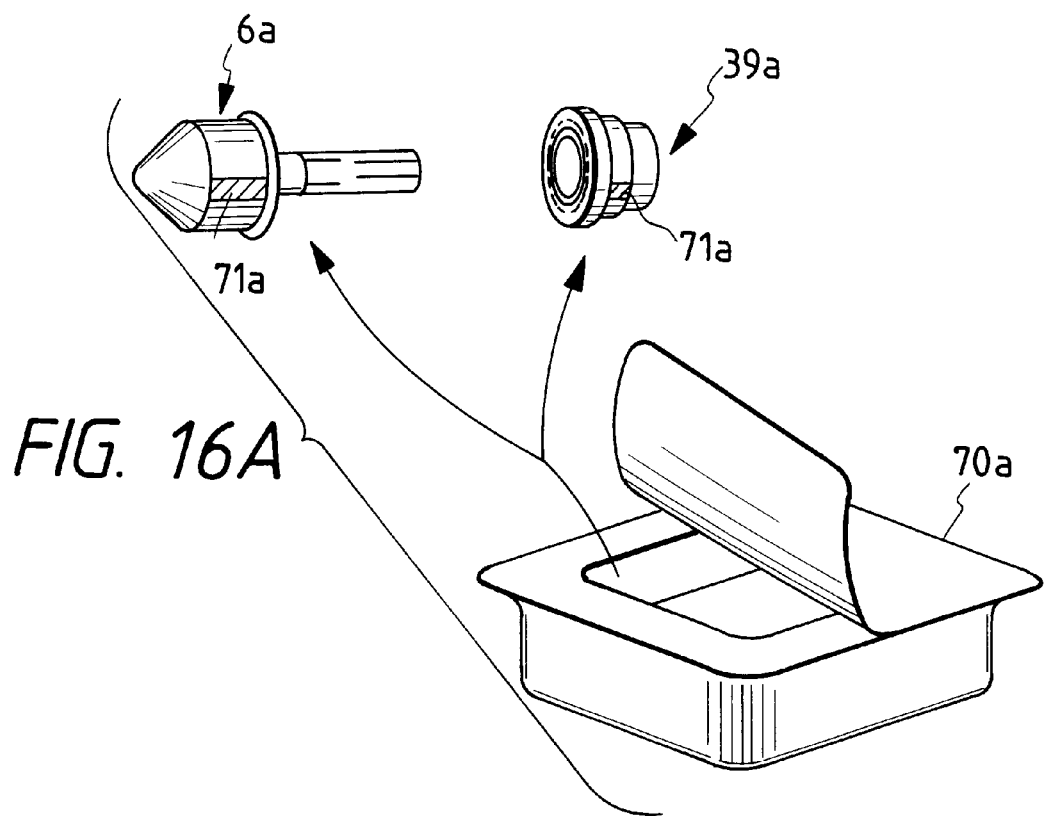
FIGS. 16A and 16B show in perspective how a staple head and an anvil head of a medical suturing apparatus according to a fifth embodiment of the invention are baled for shipment.
Figure 16B:
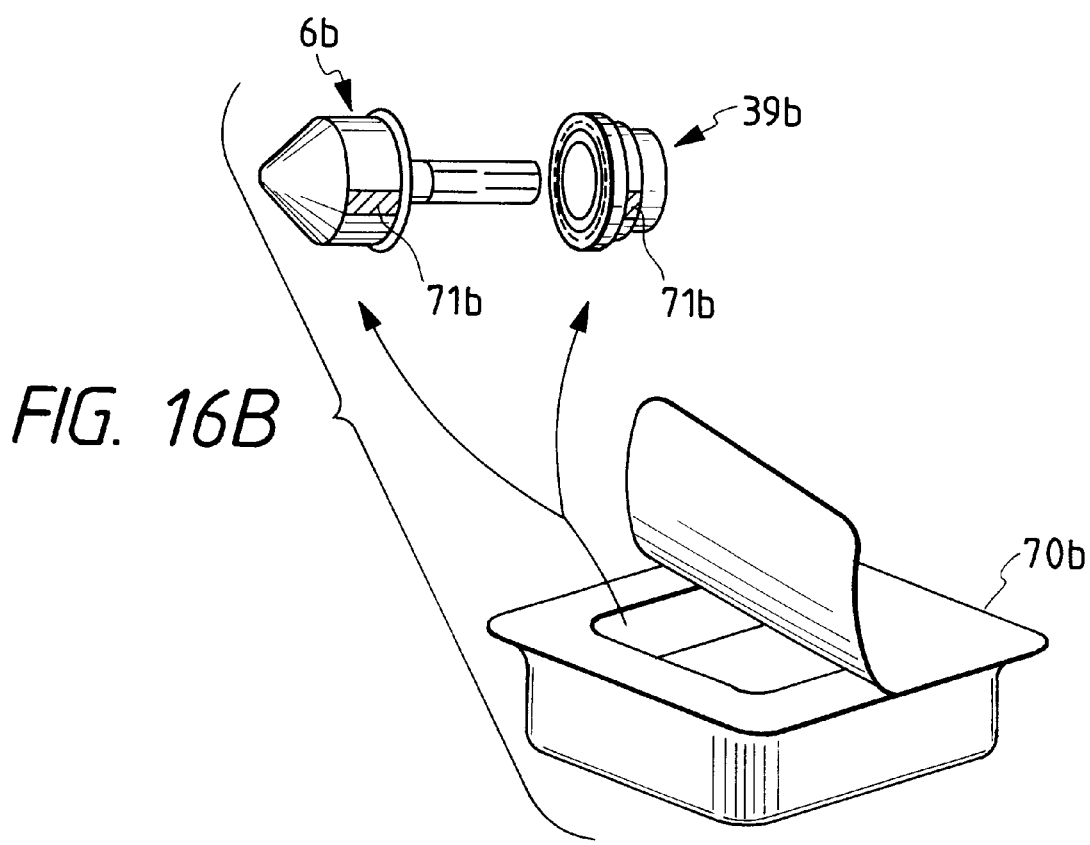

FIG. 16 shows a fifth embodiment of the invention and the structural parts which are identical to those employed in the third embodiment are identified by like numerals and will not be described in detail. The third embodiment is essentially the same as the third embodiment except for the following: staple head 6a and anvil set 39a are packed together in a bale 70a of a first size whereas staple head 6b and anvil set 39b are packed together in a bale 70b of a second size; the staple head 6a and anvil set 39a are each fitted with a size color 71a whereas the staple head 6b and anvil set 39b are each fitted with a different size color 71b.

The fifth embodiment offers the following advantage: if the staple head 6a and the anvil set 39a which are taken out of the bale 70 (see FIG. 16A) do not fit the inside diameter of the intestine to which anastomos is to be applied, the surgeon may unpack the bale 70b of a different size and use the staple head 6b and anvil set 39b which will fit the inside diameter of the tissue section. If the right combination of sizes is not known, the surgeon may refer to the size colors 71a and 71b which are provided for the respective combinations of staple head (6a or 6b) and anvil set (39a or 39b).

In addition to the advantages of the third embodiment, the fifth embodiment offers the following advantages: the staple head 6a and anvil head set 39a are packed together in the bale 70a of a first size whereas the staple head 6b and anvil set 39b are packed together in the bale 70b of a second size and, therefore, only one of the bales need be unpacked. Even if both bales are unpacked, the right combination of staple head and anvil set can be identified by referring to different size colors 71a and 71b. This eliminates inadvertent combining of a staple head of a first size with an anvil set of a second size and vice versa. The same results are achieved even if the size colors are replaced by similar devices such as other size indices and combination elements.

FIGS. 17 to 24 illustrate a medical suturing apparatus according to a sixth embodiment of the invention. FIG. 17A shows a general overall view of the medical suturing apparatus which is generally indicated by 101. The main body 102 of the apparatus is composed of an operating member 103 and an insertion member 104 extending distally from the operating member 103. The distal end of the insertion member 104 is fitted with a detachable anvil head 105. The operating member 103 comprises a rotatable adjusting knob 106, a lever 107 and a slider switch 108. A detailed construction of the operating member 103 will be described below.

Figures 17A, 17B:
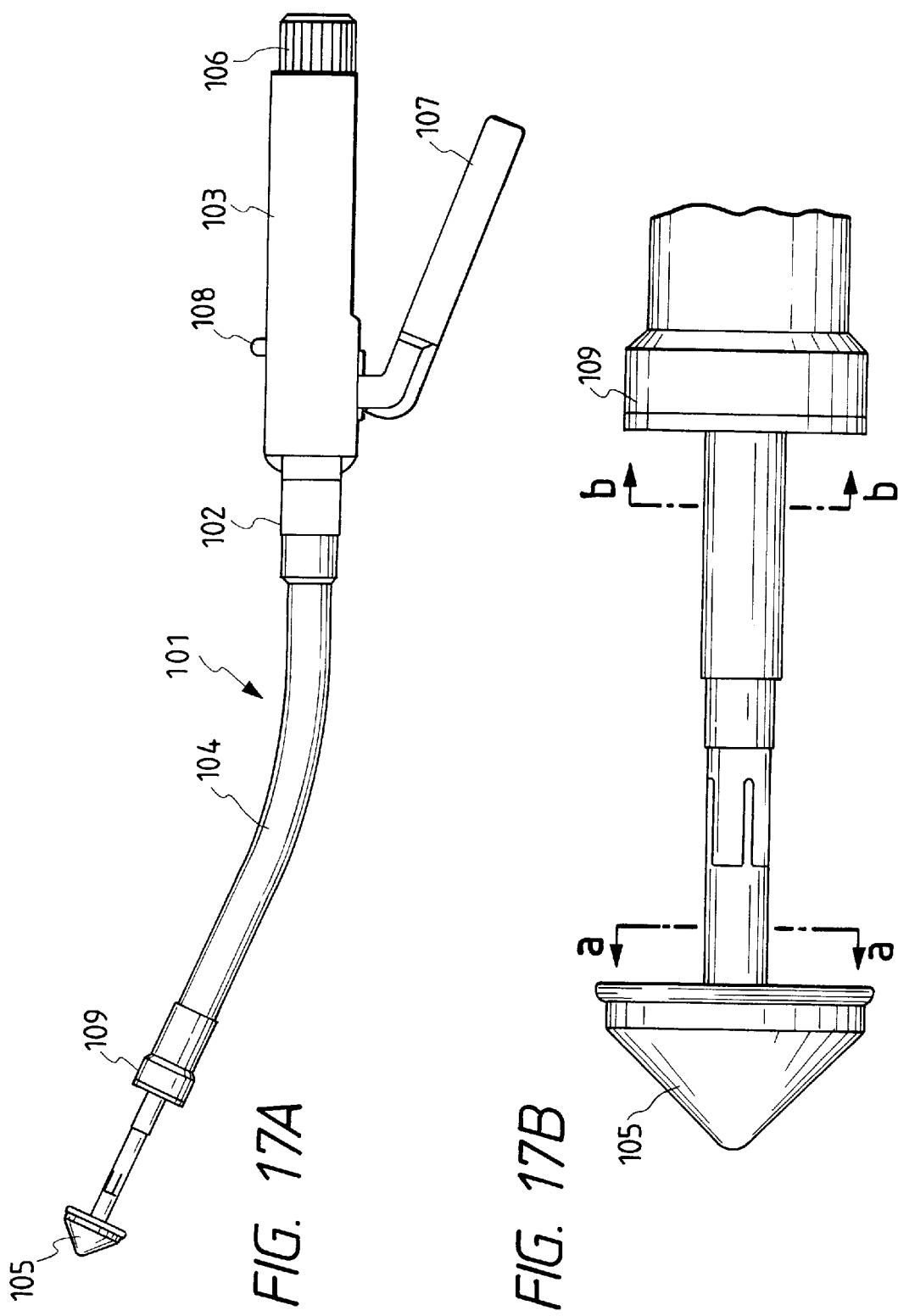
FIG. 17A shows a general overall view of a medical suturing apparatus according to a sixth embodiment of the invention.
FIG. 17B is a side view of a head of an insertion member and an anvil head of the apparatus shown in FIG. 17A.

FIG. 17B shows the construction of the distal end of the insertion member 104 which has the anvil head 105 installed on the head 109. The anvil head 105 is shown in FIG. 18A, the head of the insertion member 109 in FIG. 18B, and a cross section of the head 109 in FIG. 18C.

As is clear from FIGS. 18A to 18C, the distal end of the insertion member 104 is provided with a trocar 114 disposed in the center to serve as a guide for installing an anvil shaft 112 (to be described later) at the distal end of the insertion member 104, a tubular trocar sleeve 115 which covers the trocar 114, and outwardly flared leaf springs 116 formed by axially slotting the outer circumference of the trocar sleeve 115.

The trocar sleeve 115 and the leaf springs 116 are fixed at the basal end to the trocar 114. Inwardly projecting latches 117 are provided at the distal end of the leaf springs 116. The trocar sleeve 115 is surrounded by a tubular outer sleeve 118 which is capable of moving back and forth relative to the trocar 114.

As shown in FIG. 18B, the head of the insertion member 109 has an annular array of staple channels 120 each accommodating a staple 119. As shown in FIG. 18C, the head of the insertion member 109 has a staple pusher 123 having a plurality of rod-shaped projections 123a for direct expelling of staples 119. The rod-shaped projections 123a are inserted into the respective staple channels 120 in a ring pattern. The staple channels 120 are formed of a staple channel casing 122, which is internally provided with a cylindrical cutter 121 that is fixed to the staple pusher 123.

As shown in FIG. 19A, a rod 124 is disposed through the center of the operating member 103 and a rod screw 124a disposed at the proximal end of the rod 124 is threaded into a rotating screw 125 in the adjusting knob 106 (see FIG. 17). The rod 124 is partly provided with a safety guide 127 and a rod groove 124b whereas a trocar drive member 128 is fixed at the distal end of the rod 124; a distal edge 127a is provided at the distal end of the safety guide 127.

The safety guide 127 is in contact with the top surface 130a of a safety lock 130 and the safety lock 130 is mounted to a casing 131 in such a way that it is rotatable about an axis parallel to the rod 124. An outer sleeve drive member 132 is disposed above and close to the rod 124 and a slider switch 108 is disposed at the proximal end of the outer sleeve drive member 132 in such a way that it is capable of moving back and forth relative to the casing 131. Provided below the slider switch 108 is a slider latch 108a which is free to come into or out of engagement with the rod groove 124b.

A trigger 133 is fixed to the lever 107 and this is mounted to the casing 131 in such a way that it is free to rotate about a pin 134. A coil spring 135 is wound about the pin 134 and the two ends of the coil spring 135 are mounted to the trigger 133 and the casing 131, respectively. The coil spring 135 urges the trigger 133 in such a direction that the lever 107 is opened. Normally, a trigger lock 130b provided on the safety lock 130 is in contact with a trigger edge 133b of the trigger 133 so as to restrict the action of the latter.

A staple drive member 136 is disposed close to the top surface of the outer sleeve drive member 132 and a trigger receptacle 137 is provided at the proximal end of the staple drive member 136, with a trigger end 133a in the upper part of the trigger 133 being mounted to the trigger receptacle 137. The casing 131 is also provided with an indicator lever 138 which is distally urged by means of an indicator spring 139, such that the action of the indicator lever 138 can be observed through an indicator window 131a made in the casing 131.

Figure 20:
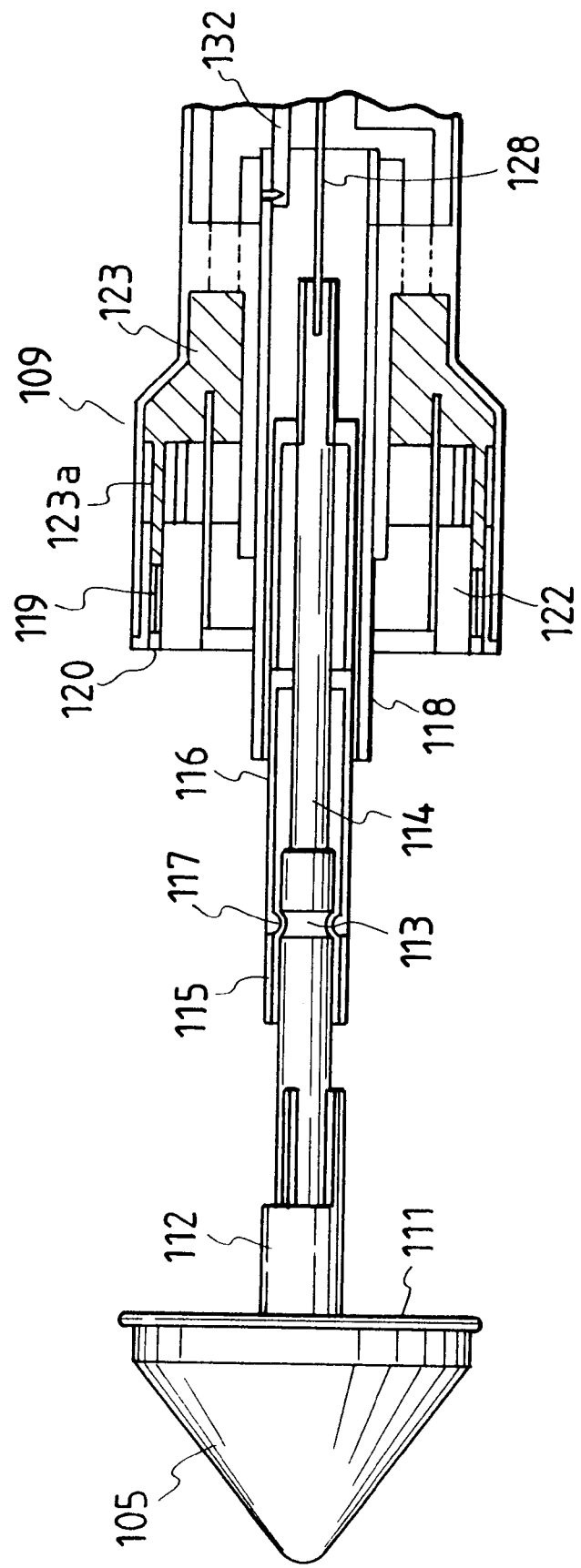
FIG. 20 is a longitudinal sectional side view of the head of an insertion member of the medical suturing apparatus according to the sixth embodiment of the invention.
Figure 21:
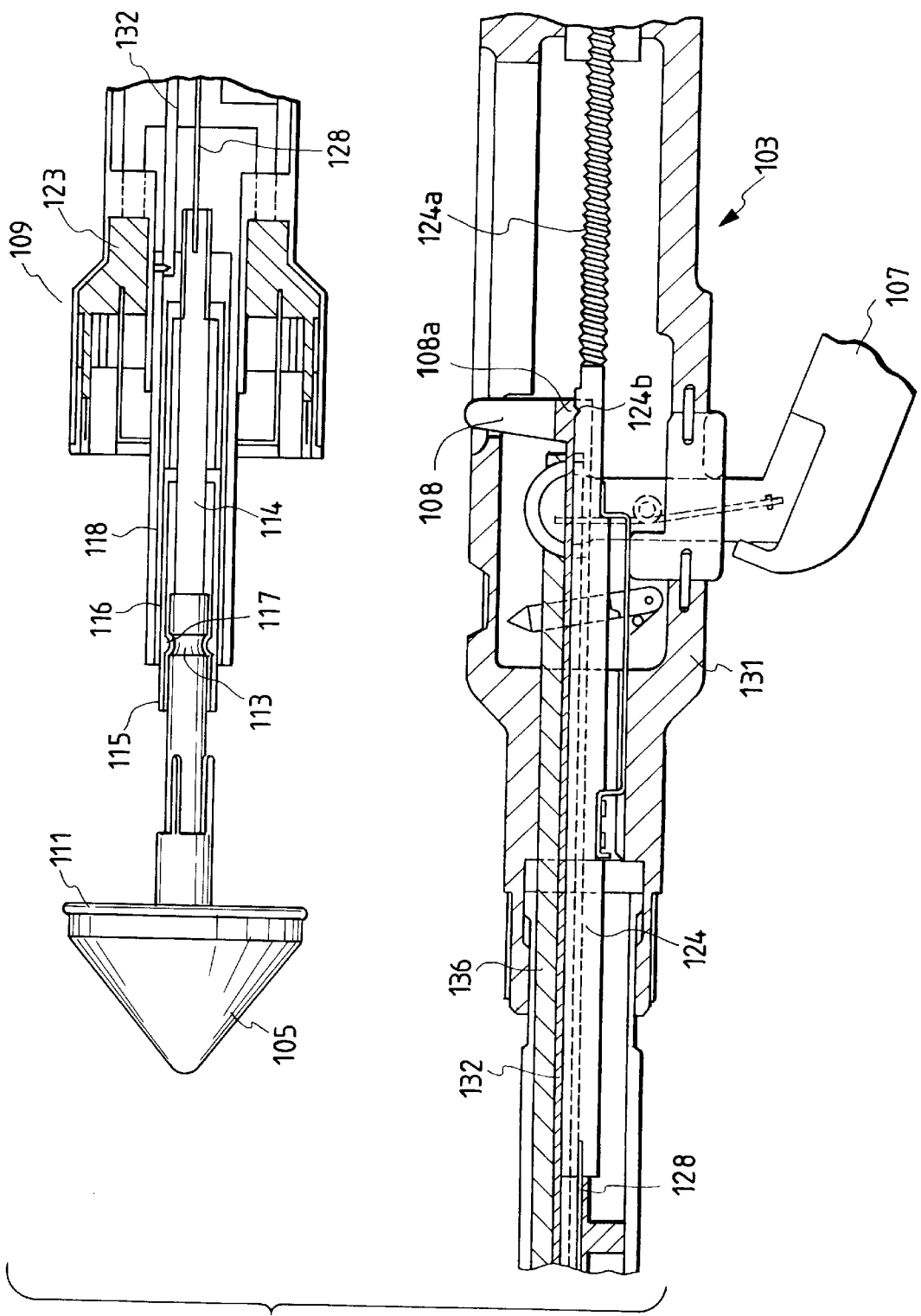
FIG. 21 is a longitudinal sectional side view of the head of an insertion member and an operating member, illustrating a phase of the operation of the medical suturing apparatus according to the sixth embodiment of the invention.

As shown in FIGS. 19 and 20, the insertion member 104 contains in it the following parts: the trocar drive member 128 extending through the center; a guide 128a for supporting the trocar drive member 128; the outer sleeve drive member 132 provided above the trocar drive member 128; and the staple drive member 136 in contact with the interior of the insertion member 104. The individual drive members are capable of moving back and forth independently of each other and in the interior of the head of the insertion member 109, the trocar drive member 128 is fixed to the trocar 114, the staple drive member 136 to the staple pusher 123, and the outer sleeve drive member 132 to the outer sleeve 118. The anvil head 105 which is to be installed on the head of the insertion member 109 is provided with an anvil 111 having slots 111a for clinching staples 119 (see FIG. 18A), tubular anvil shaft 112 for coupling the anvil head 105 to the trocar 114, and circular grooves 113 formed at the proximal end of the anvil shaft 112 and which are free to come into or out of engagement with the latches 117 (see FIG. 18c).

Having described above the construction of the suturing apparatus according to the sixth embodiment of the invention, we now describe how it is operated.

First, the anvil head 105 is inserted into an end of a tissue section of a tubular structure, say, the intestine and said one end is purse-string sutured around the anvil shaft 12. In addition, the insertion member 104 of the main body 102 is inserted into the other end of the tissue section and said other end is also purse-string sutured around the outer sleeve 118.

Thereafter, the anvil shaft 112 is inserted into the trocar sleeve 15 using the trocar 114 as a guide, whereupon the leaf springs flex outwardly, causing the latches 117 to come into engagement with the circular grooves 113 (see FIG. 20). If the slider switch 108 of the operating member 103 is moved distally, the slider latch 108a in the operating member 103 comes into engagement with the rod groove 124b on the rod 124 (see FIG. 21).

In addition, the distal movement of the slider switch 108 will cause the outer sleeve drive member 132 to be moved distally, whereupon the outer sleeve 118 is moved distally to cover the leaf springs 116. In this state, the anvil head 105 will not be disconnected from the head of the insertion member 109 since the outer sleeve 118 will restrain the leaf springs 116 from flexing outwardly (see FIG. 21).

In the next step, the adjusting knob 106 of the operating member 103 is rotated, whereupon the rod 124 is gradually retracted toward the operator under the action of the rod screw 124a and the rotating screw 125. Since the trocar drive member 128 is fixed at the distal end of the rod 124, the anvil head 105 is moved toward the head of the insertion member 109. On this occasion, the distal edge 127a of the safety guide 127 comes into engagement with the indicator edge 138a, whereupon the indicator lever 138 is actuated to give the operator a visual signal for the distance between the anvil head 105 and the head of the insertion member 109. At the same time, the outer sleeve 118 is retracted since the slider switch 108a is in engagement with the rod groove 124b (see FIG. 22). When the distance between the anvil head 105 and the head of the insertion member 109 has reached an appropriate value for performing anastomosis, the safety guide 127 in the operating member 103 is moved toward the proximal end by means of the top surface 130a of the safety lock 130. If the safety lock 130 is rotated, the trigger edge 133b comes out of engagement with the trigger lock 130b and the operator can now grip the lever 107.

If the operator grips the lever 107, the trigger 133 will rotate about the pin 134 and the trigger end 133a moves the trigger receptacle 137 distally. Hence, a compressive force is transmitted through the staple drive member 136 and staple pusher 123 to reach the rod-shaped projections 123a, which then cause staples 119 to be ejected form the staple channels 120 and the ejected staples 119 are clinched by the slots 111a in the anvil 111. At the same time, the cylindrical cutter 121 severs the excess tissue of the intestine inside the staple line to complete the anastomotic operation (see FIG. 23).

If the slider switch 108 of the operating member 103 is slid toward the operator 25, the anvil head 105 is moved toward the head of the insertion member 109 or after the end of adjustment of the distance between the anvil head 105 and the head of the insertion member 109 or at any other position of the anvil head 105, the slider latch 108a is disengaged from the rod groove 124a and the outer sleeve drive member 132 is move toward the operator.

Figure 24:
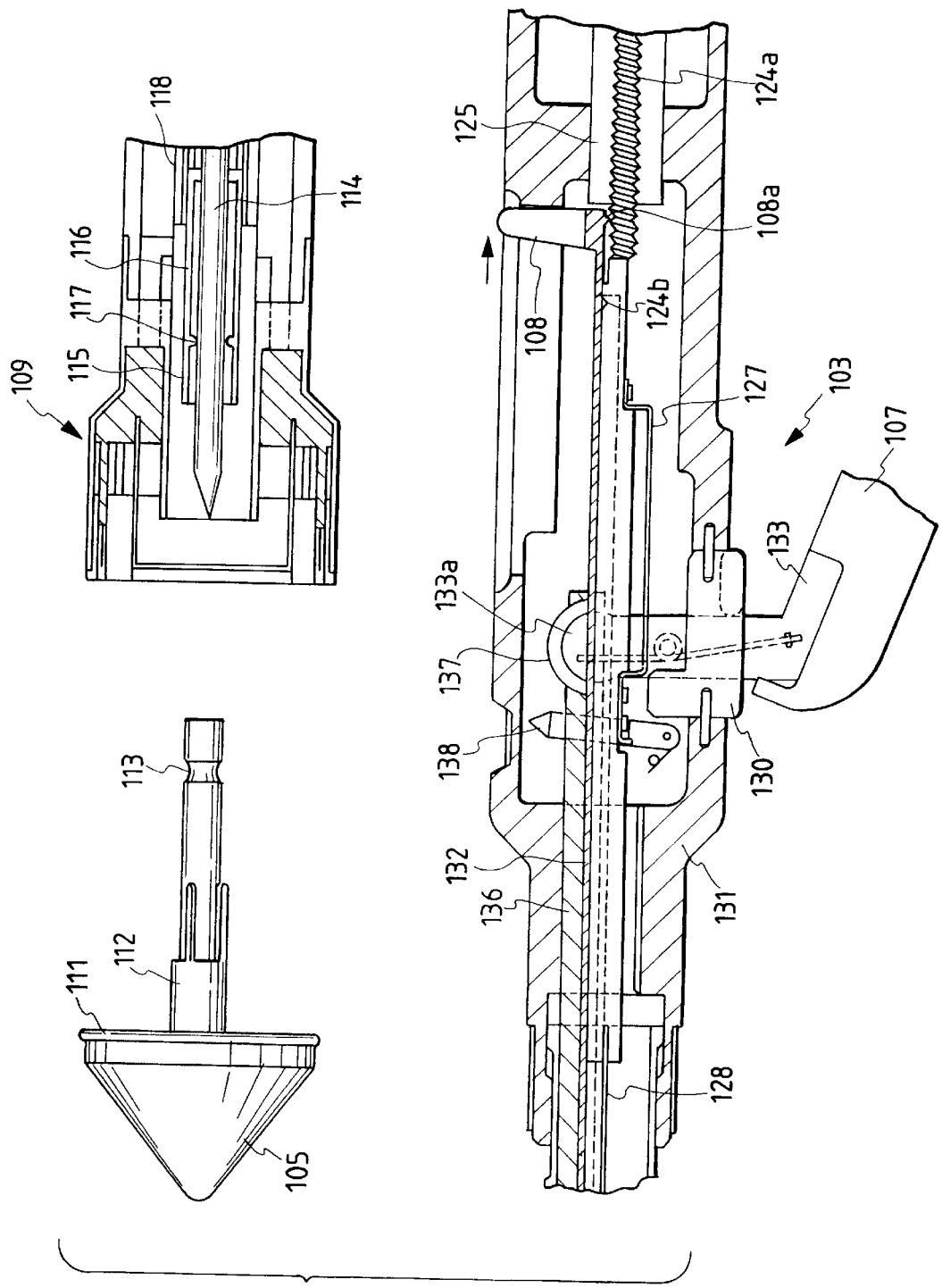
FIG. 24 is a longitudinal sectional side view of the head of an insertion member and the operating member, illustrating yet another phase of the operation of the medical suturing apparatus according to the sixth embodiment of the invention.

As a result, the outer sleeve 118 which has covered the leaf springs 116 are moved toward the operator and the leaf springs 116 are now capable of flexing outwardly; in this state, the anvil head 105 can be disconnected from the head of the insertion member 109 and a new anvil head 105 can be installed on the head of the insertion member 109 (see FIG. 24).

According to the sixth embodiment of the invention, the anvil head 105 can be fixed in position immediately after it is fitted to the head of the insertion member 109 and, hence, there is no possibility that the anvil head 105 is dislodged from the head of the insertion member 109 at an unintended position as the anvil head 105 is retracted toward the head of the insertion member 109. In addition, if any trouble such as twisting of the intestine occurs during adjustment of the distance between the anvil head 105 and the head of the insertion member 109, the anvil head 105 can immediately be disconnected form the head of the insertion member 109; thus, the medical suturing apparatus according to the sixth embodiment of the invention is very easy to manipulated.

FIGS. 25 and 26 show a seventh embodiment of the invention and the structural parts which are identical to those employed in the sixth embodiment are identified by like numerals and will not be described in detail. The anvil shaft 112 of the anvil head 105 in the seventh embodiment does not have the circular grooves 113 which are provided in the sixth embodiment and, instead, the shaft 112 has external ribs 140 and internal ribs 144 which are formed on the inner surface of the shaft to project radially inwardly.

The trocar sleeve 115 and the outer sleeve 118 used in the sixth embodiment are not provided within the head of the insertion member 109 according to the seventh embodiment; instead, the head 109 contains in it a rotating shaft 142 internally provided with a double thread 143 and a rotating shaft drive member 145 which transmits the rotation of the adjusting knob 106 of the operating member 103 to the rotating shaft 142.

In addition, a trocar 114 is provided that has slits 141 extending parallel to the axis of the insertion member 104. Further in addition, the slider switch 108 and the outer sleeve drive member 132 which are employed in the sixth embodiment are absent from the seventh embodiment. Except for these and other points described above, the seventh embodiment is essentially the same as the sixth embodiment.

Figure 27A:
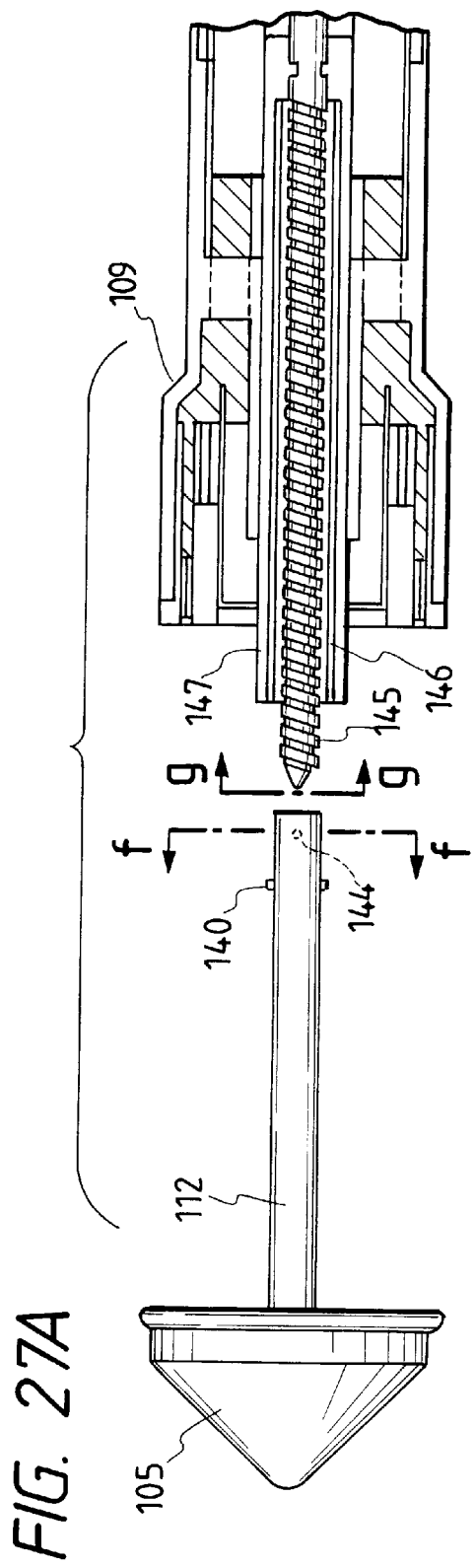
FIG. 27A is a longitudinal sectional side view of the head of an insertion member according to a modification of the seventh embodiment of the invention.
Figures 27B, 27C:
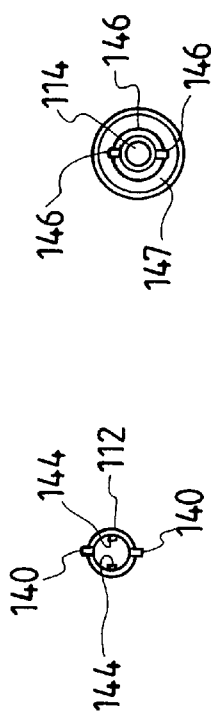
FIG. 27B is a cross section taken on line f—f of FIG. 27A.
FIG. 27C is a cross section taken on line g—g of FIG. 27A.

A modification of the seventh embodiment is shown in FIG. 27, in which the trocar 114 is externally provided with a double thread 145 to be rendered rotatable and an equivalent of the rotating shaft 142 is formed of a sleeve 147 having safety guides 146 and the internal ribs 144 are formed on the inner surface of the anvil shaft 112.

When mounting the anvil head 105 to the head of the insertion member 109 in the seventh embodiment, the trocar 114 is inserted into the anvil shaft. 112, with the internal ribs 114 in the anvil shaft 112 being in registry with the slits 141, until it contacts the distal end of the anvil shaft (see FIG. 26A). When the adjusting knob 106 of the operating member 103 is rotated, the rotation is transmitted to the rotating shaft 142 via the rotating shaft drive member 145. The rotation of the rotating shaft 142 as combined with the external ribs 140 in engagement with the double internal thread 143 causes the anvil head 105 to be slowly moved toward the head of the insertion member 109; however, the combined action of the internal ribs 144 and the slits 141 will prevent the anvil head 105 from rotating (see FIG. 26B).

If the distance between the anvil head 105 and the head of the insertion member 109 is determined, the subsequent procedure will be the same as in the sixth embodiment. In the modification shown in FIG. 27, the rotation of the trocar 114 in engagement with the internal ribs 144 will retract the anvil shaft 112 such that the anvil head 105 is moved toward the head of the insertion head 109 while the external ribs 140 combine with the safety guides 146 to prevent the rotation of the anvil head 105.

Because of these structural features, the seventh embodiment has the advantage that as soon as the anvil head 105 is installed on the head of the insertion member 109, it is secured against disconnection from the head 109. Since there is no possibility of the anvil head 105 to be dislodged accidentally during the anastomotic operation, the medical suturing apparatus of the invention can be manipulated efficiently. Similar results are attained in the modification of the seventh embodiment which is shown in FIG. 27.

Figure 28A:
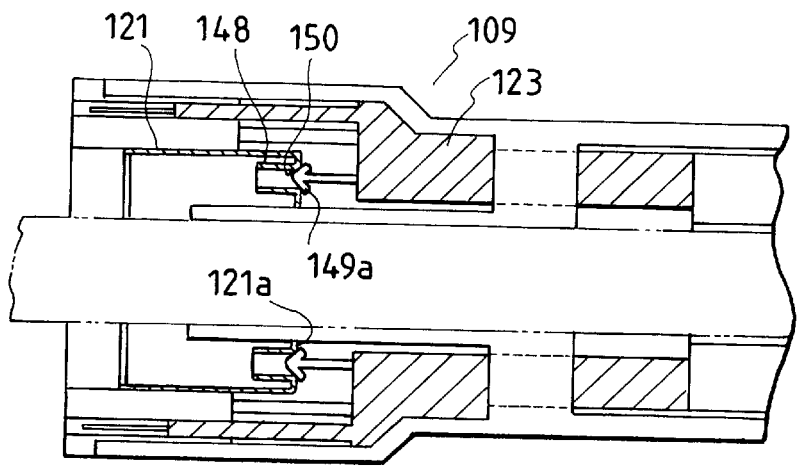
FIGS. 28A, 28B and 28C are longitudinal sectional side views showing in sequence the operation of the head of an insertion member according to an eighth embodiment of the invention.
Figure 28B:
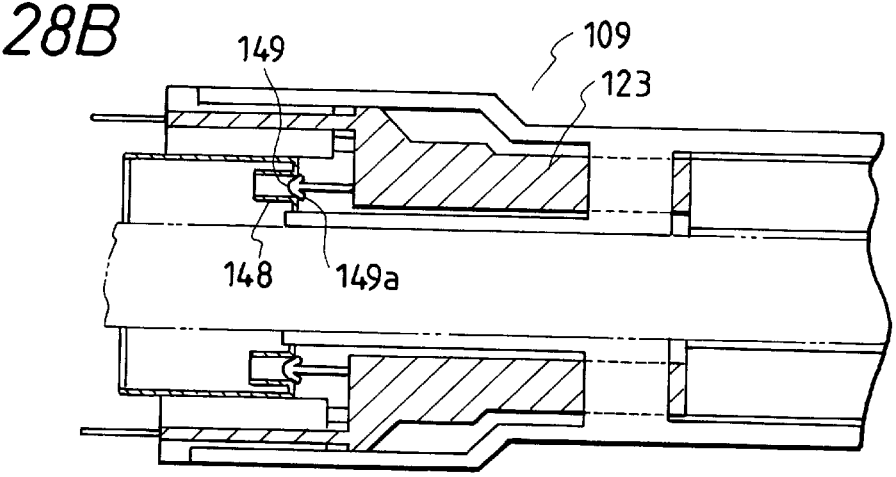
Figure 28C:
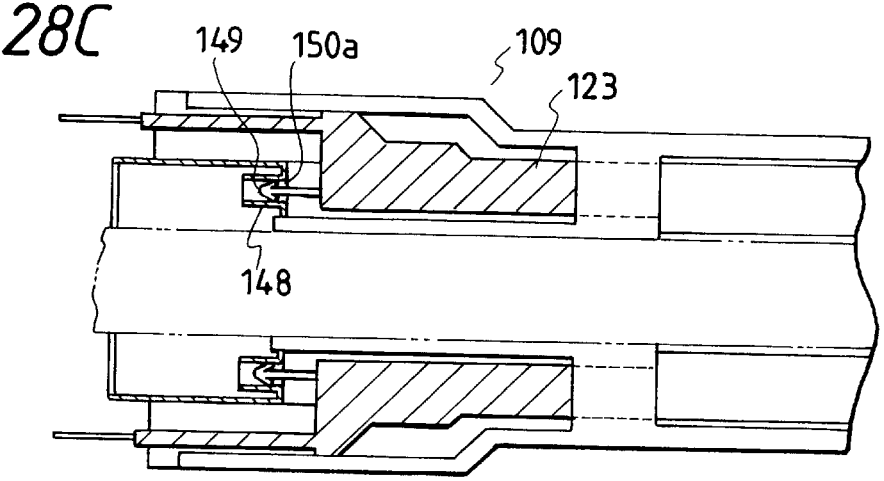
Figure 29A:
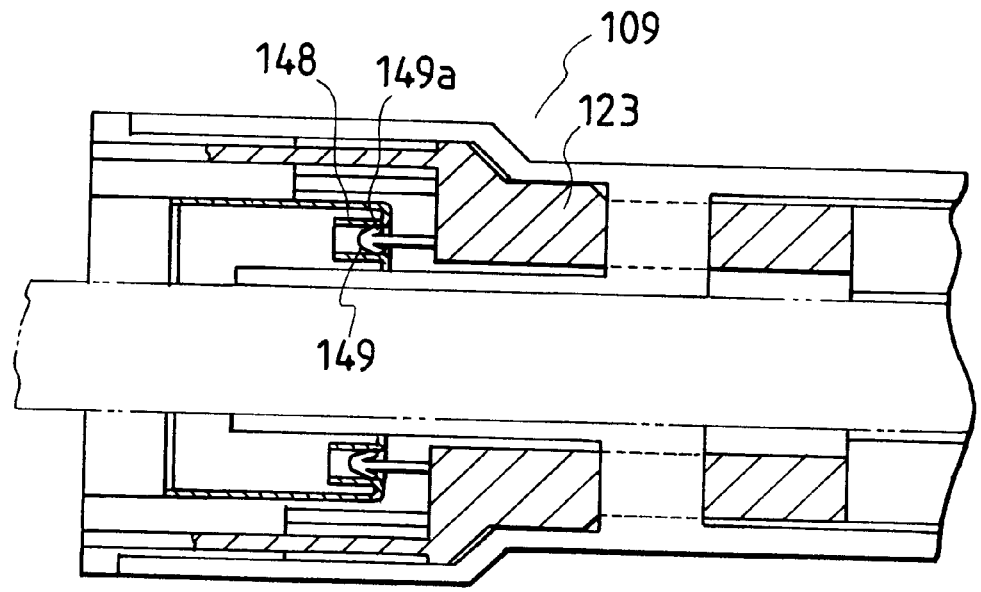
FIGS. 29A and 29B are longitudinal sectional side views showing in sequence another operation of the head of an insertion member.
Figure 29B:
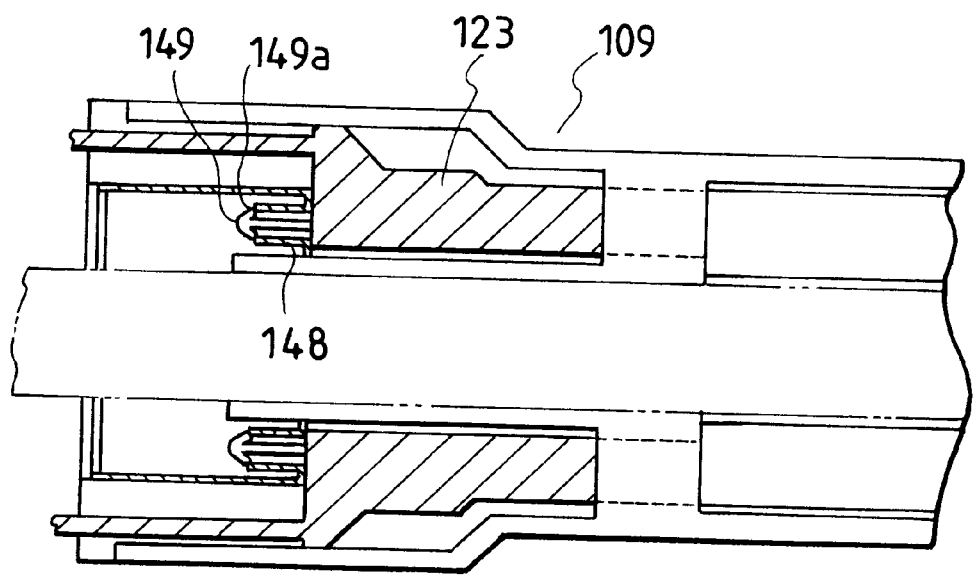

FIGS. 28 and 29 show an eighth embodiment of the invention and the structural parts which are identical to those employed in the sixth embodiment are identified by like numerals and will not be described in detail. According to FIG. 28, there are provided within the head of the insertion member 109 a plurality of holes 150 made in the bottom 121a of the cylindrical cutter 121 and latching sleeves 148 which have a larger inside diameter than the holes 150 and which are arranged coaxially with said holes 150.

Each hole 150 has a hole edge 150a formed on the inner circumference. The staple pusher 123 is provided with arrow-shaped latches 149 fixed coaxially with the latching sleeves 148 and each of the arrow-shaped latches 149 has fingers 149a. The cylindrical cutter 121 is adapted to be capable of moving back and forth relative to the staple pusher 123 in the axial direction of the head of the insertion member 109. Except for these and other points described above, the eighth embodiment is essentially the same as the sixth embodiment.

Description is therefore made of only the action of ejecting the cylindrical cutter 121. In the initial state (see FIG. 28A), the operator grips the lever 107 of the operating member 103, whereupon the staple pusher 123 is urged distally. Then, the arrow-shaped latches 149 are inserted into the holes 150 and the fingers 149 come into engagement with the bottom 121a of the cutter 121, causing the latter to be moved distally (see FIG. 28B).

If the operator continues to grip the lever 107, the staple pusher 123 is further moved distally and the continued action of the arrow-shaped latches 149 will keep the cylindrical cutter 121 moving. When the blade of the cylindrical cutter 121 contacts the washer (not shown) on the anvil head side, the developing resistance will cause an elastic deformation of the arrow-shaped latches 149, which then pass through the holes 150 to enter the latching sleeves 148 (see FIG. 28C).

After firing the staples 119, the operator stops gripping the lever 107, whereupon the staple pusher 123 is retracted toward the operator. Since the fingers 149a of the arrow-shaped latches 149 come into engagement with the hole edges 150a in the latching sleeves 148, the cylindrical cutter 121 is also retracted toward the operator (see FIG. 29A).

When the operator grips the lever 107 again, the staple pusher 123 is moved distally and so are the arrow-shaped latches 149. Because of their shape, the moving latches 149 slide along the inner surfaces of the latching sleeves 148 to eventually pass through them, so the cylindrical cutter 121 will not project from the head of the insertion member 109. Since the arrow-shaped latches 149 are positioned on the distal end of the latching sleeves 148, no part of the cylindrical cutter 121 will be exposed as such from the head of the insertion member 109 (see FIG. 29B).

The conventional medical suturing apparatus have had a safety problem in that if the lever is gripped after firing of the staples, the cylindrical cutter will be ejected. However, this problem is absent from the suturing apparatus according to the eighth embodiment since the cylindrical cutter 121 will not be ejected even if the lever is gripped after use in anastomosis.

FIGS. 30 to 32 show a ninth embodiment of the invention and the structural parts which are identical to those employed in the sixth embodiment are identified by like numerals and will not be described in detail. As shown in FIGS. 30A and 30C, the suturing apparatus according to the ninth embodiment has a trigger lock 155 provided on the trigger edge 133b within the operating member 103 in such a way that it is free to rotate about a pin 154 while it is urged with a coil spring 153.

The lead of the insertion member 109 is shown in FIG. 30B; leaf spring latches 156 are normally provided on selected inner surfaces of the staple channel casing 122 in such a way that they are elastically deformed by the outer circumference of the cylindrical cutter 121. Except for these and other points described above, the ninth embodiment of the invention is essentially the same as the sixth embodiment.

As in the sixth embodiment, if the distance between the anvil head 105 and the head of the insertion member 109 has reached an appropriate value for anastomosis, the safety lock 130 can be released. If the operator grips lever 107, staples 119 are expelled and clinched by the slots 111a in the anvil 111. At the same time, the cylindrical cutter 121 is ejected to cut the excess tissue inside the staple line, whereby the anastomotic operation is completed (see FIG. 31B).

The state within the operating member 103 after the firing of staples 119 is shown in FIGS. 31A and 31C. If the operator grips the lever 107, the trigger 133 is rotated about the pin 134, whereupon the trigger lock 155 which has been in engagement with the trigger edge 133b rotates about the pin 154 under the elastic force of the coil spring 153. FIG. 31C shows the trigger lock 155 disengaged from the trigger edge 133b.

If the operator releases the grip on the lever 107, the trigger 133 will tend to revert to the initial state (i.e., before the expelling of staples) under the elastic force of the coil spring 135. In fact, however, the trigger lock 155 has rotated under the elastic force of the coil spring 153, so the trigger 133 will rotate without being stopped by the trigger edge 133b and, as a result, the trigger receptacle 137 will be moved toward the operator (see FIG. 32A).

The trigger receptacle 137 is provided on the staple drive member 136, so needless to say, the staple drive member 136 and the staple pusher 123 within the head of the insertion member 109 are also moved toward the operator and so is the cylindrical cutter 121 fixed to the staple pusher 123. FIG. 32B shows the staple pusher 123 as it has been moved toward the operator; obviously, the leaf spring latches 156 which were elastically disposed on the outer circumference of the cylindrical cutter 121 before firing of the staples 119 flex inwardly since the cylindrical cutter 121 has moved to the retracted position.

The suturing apparatus of the ninth embodiment of the invention has the advantage that even if the lever 107 is gripped after the firing of the staples 119, the leaf spring latches 156 will contact the blade of the cylindrical cutter 121 to thereby prevent it from projecting beyond the head of the insertion member 109. This is also the case with the staple expelling rod-shaped projections 123a since they are provided on the staple pusher 123 to which the cylindrical cutter is fixed (see FIG. 32C).

Thus, in addition to the advantages of the eighth embodiment, the suturing apparatus of the ninth embodiment offers an advantage in safety in that the rod-shaped projections 123a which are direct means of firing the staples 119 will not protrude from the head of the insertion member 109. Even if the lever 107 being withdrawn from a section of the intestine is gripped inadvertently, the normal tissue will not be affected at all.

As described on the foregoing pages, the medical suturing apparatus according to the first aspect of the invention has an anvil head provided at the distal end of the main body and a staple head having a plurality of staples disposed therein is provided in a position opposed to the anvil head and this offers the advantage that even if the lever is gripped when performing anastomosis on tubular structures such as the intestine and esophagus, no staples will be expelled from the staple head or the cutter will not be ejected unless the staple head is installed at the distal end of the main body. Therefore, the unnecessary firing of staples and the hazard of the cutter are significantly reduced. In addition, the running cost of hospitals is also reduced by using the main body repeatedly after replacing the staple head by a new one.

According to the second aspect of the invention, there is provided a medical suturing apparatus in which an anvil head can be fixed in position immediately after it is installed on a trocar at the distal end of the insertion member when performing anastomosis on tubular structures such as the intestine and esophagus. Hence, there is no possibility that the anvil is dislodged in an unintended position as it is moved toward the head of the insertion member. In addition, the manipulability of the suturing apparatus is improved since the anvil head can be disconnected as soon as there occurs a trouble such as twisting of the intestine during adjustment of the distance between the anvil head and the head of the insertion member. Further in addition, the cylindrical cutter will not project from the head of the insertion member even if the lever of the operating member is inadvertently gripped after the firing of staples. This is a salient advantage in safety since no part of the normal tissue will be damaged by the suturing apparatus being withdrawn from the intestine.

What is claimed is:

1. A medical suturing apparatus comprising:

a first actuating element;

a second actuating element;

an operating member having an adjusting mechanism coupled to said first actuating element, a gripping mechanism releasably coupled to said second actuating element, and a manually operable release switch for coupling said gripping mechanism to said second actuating element when the release switch is in one position and for decoupling said gripping mechanism from said second actuating element when the release switch is in another position;

an insertion member coupled at a first end to said operating member and extending therefrom to be inserted into a body cavity, said first actuating element and said second actuating element extending through said insertion member; and a suturing member positioned at a second end of said insertion member, said suturing member being operated by manipulation of said adjusting mechanism and said gripping mechanism, said suturing member comprising:

a first head engaging the second end of said insertion member; and a second head detachably coupled to said first head and which is actuated by said first actuating element to move between a first position and a second position, said second position being closer to said first head than said first position, the manipulation of said gripping mechanism being restricted in said first position, and said second head comprising:

a staple expelling mechanism coupled to said second actuating element; and a casing having a plurality of staples disposed therein and being slidable relative to said staple expelling mechanism, said casing being coupled to said first actuating element; wherein said first actuating element stops said casing from moving toward said first head while said second actuating element actuates said staple expelling mechanism.

2. A medical suturing apparatus according to claim 1, wherein the first head of said suturing member comprises an anvil head.

3. A medical suturing apparatus according to claim 2, wherein each of said staples comprises a couple of legs each having a sharp tip and a base connecting said legs to each other, said legs being disposed to face said anvil head and said sharp tips of said legs directing to said anvil head.

4. A medical suturing apparatus according to claim 1, wherein said plurality of staples move between said first and second positions.

5. A medical suturing apparatus according to claim 4, wherein each of said staples comprises a base and at least two legs extending from said base, the length of each of said legs being smaller than the distance between said first and second heads at said first position but greater than the distance between said first and second heads at said second position.

6. A medical suturing apparatus according to claim 1, further comprising a cutter installed on either one of said first and second heads and operating at said second position.

7. A medical suturing apparatus according to claim 6, further comprising a plate for receiving said cutter disposed on the head other than the head on which said cutter is installed.

8. A medical suturing apparatus according to claim 7, wherein said receiving plate is installed on either one of said first and second heads and the other of said first and second heads is provided with said cutter, with radially positioning means being provided on the head which is fitted with said receiving plate.

9. A medical suturing apparatus according to claim 7, wherein said cutter is installed on either one of said first and second heads and the other of said first and second heads is provided with said receiving plate, with radially positioning means being provided on the head which is fitted with said cutter.

10. A medical suturing apparatus according to claim 6, further comprising a mechanism for prohibiting the ejecting of said cutter from said casing after said staples have been expelled.

11. A medical suturing apparatus according to claim 1, wherein said staple expelling mechanism, after having expelled said staples, is retracted into the casing from the position in said staple expelling mechanism was initially accommodated.

12. A medical suturing apparatus according to claim 11, further comprising a mechanism for prohibiting the ejecting of said cutter from said casing after said staples have been expelled.

13. A medical suturing apparatus according to claim 1, wherein said gripping mechanism is releasably coupled to said second actuating element via a latch located in said operating member, one part of the latch being coupled to said gripping element, and another part of the latch making coupled contact with said second actuating element only when the latch is in a lowered position, the latch being lowered by the release switch when the release switch is in the one position and the latch being raised by the release switch when the release switch is in the other position.

14. A medical suturing apparatus according to claim 1, wherein said gripping mechanism is releasably coupled to said second actuating element via a latch located in said operating member, one part of the latch being coupled to said gripping element, and another part of the latch making coupled contact with said second actuating element only when the latch is in a lowered position, the latch being lowered by the release switch when the release switch is in the one position and the latch being raised by the release switch when the release switch is in the other position.

* * * * *